(12) United States Patent
Ferentz et al.

(10) Patent No.: US 11,908,553 B2
(45) Date of Patent: Feb. 20, 2024

(54) APPARATUS AND METHOD FOR EMERGENCY RESPONSE DATA ACQUISITION AND RETRIEVAL

(71) Applicant: RAPIDSOS, INC., New York, NY (US)

(72) Inventors: Zvika Ferentz, Rye Brook, NY (US); William Pellegrini, Graham, WA (US); Gabe Mahoney, Brooklyn, NY (US); Nicholas Edward Horelik, Long Island City, NY (US); Jee Yoon Choi, Brooklyn, NY (US)

(73) Assignee: RAPIDSOS, INC., New York, NY (US)

( * ) Notice: Subject to any disclaimer, the term of this patent is extended or adjusted under 35 U.S.C. 154(b) by 704 days.

(21) Appl. No.: 16/786,962

(22) Filed: Feb. 10, 2020

(65) Prior Publication Data

US 2020/0258606 A1     Aug. 13, 2020

Related U.S. Application Data

(60) Provisional application No. 62/923,093, filed on Oct. 18, 2019, provisional application No. 62/804,131, filed on Feb. 11, 2019.

(51) Int. Cl.
  *G16H 10/60* (2018.01)
  *G06Q 50/26* (2012.01)
  *G06F 16/245* (2019.01)

(52) U.S. Cl.
  CPC ........... *G16H 10/60* (2018.01); *G06F 16/245* (2019.01); *G06Q 50/265* (2013.01)

(58) Field of Classification Search
  CPC ..... G16H 10/60; G06F 16/245; G06Q 50/265
  (Continued)

(56) References Cited

U.S. PATENT DOCUMENTS

2001/0051879 A1* 12/2001 Johnson ................ H04L 63/102
                                                       707/999.001
2014/0025394 A1*  1/2014 Aoki ...................... G16H 40/67
                                                       705/2
(Continued)

FOREIGN PATENT DOCUMENTS

JP         2014109826 A    6/2014
JP           5711117 B2    4/2015
(Continued)

OTHER PUBLICATIONS

Wikipedia, Software as a service, May 23, 2018, https://en.wikipedia.org/w/index.php?title=Software_as_a_service&oldid=842635139 (Year: 2018).*

(Continued)

*Primary Examiner* — Joshua B Blanchette
(74) *Attorney, Agent, or Firm* — Cygan Law Offices PC; Joseph T. Cygan

(57) ABSTRACT

A disclosed method includes receiving an emergency data request with a patient identifier; retrieving protected data from a database corresponding to the patient identifier; and displaying the protected data on an emergency responder device display. Another disclosed method includes pushing a plurality of anonymized candidate profiles associated with a device identifier to an emergency network entity, in response to initiation of an emergency session by a device having the device identifier where the anonymized candidate profiles provide anonymized patient information without exposing protected data related to a patient and correspond to a non-anonymized medical profile for the patient; receiving a request from the emergency network entity for a specific non-anonymized medical profile corresponding to one of the plurality of anonymized candidate profiles; and providing a non-anonymized medical data profile corre- (Continued)

sponding to the specific anonymized candidate profile to the emergency network entity in response to the request.

16 Claims, 15 Drawing Sheets

(58) Field of Classification Search
USPC .......................................................... 705/2, 3
See application file for complete search history.

(56) References Cited

U.S. PATENT DOCUMENTS

2015/0288797 A1* 10/2015 Vincent .................. G16H 10/60
455/404.2
2015/0310174 A1* 10/2015 Coudert .................. G06F 16/22
726/5
2016/0142894 A1* 5/2016 Papakonstantinou .. G16H 40/67
455/404.1

FOREIGN PATENT DOCUMENTS

| KR | 101582967 B1 | 1/2016 |
| KR | 1020180111484 A | 10/2018 |
| WO | WO2009147598 A1 | 12/2009 |

OTHER PUBLICATIONS

PCT ISR; PCT/US2020/017566; Jun. 9, 2020.
PCT Written Opinion of the ISA; PCT/US2020/017555; dated Jun. 9, 2020.

* cited by examiner

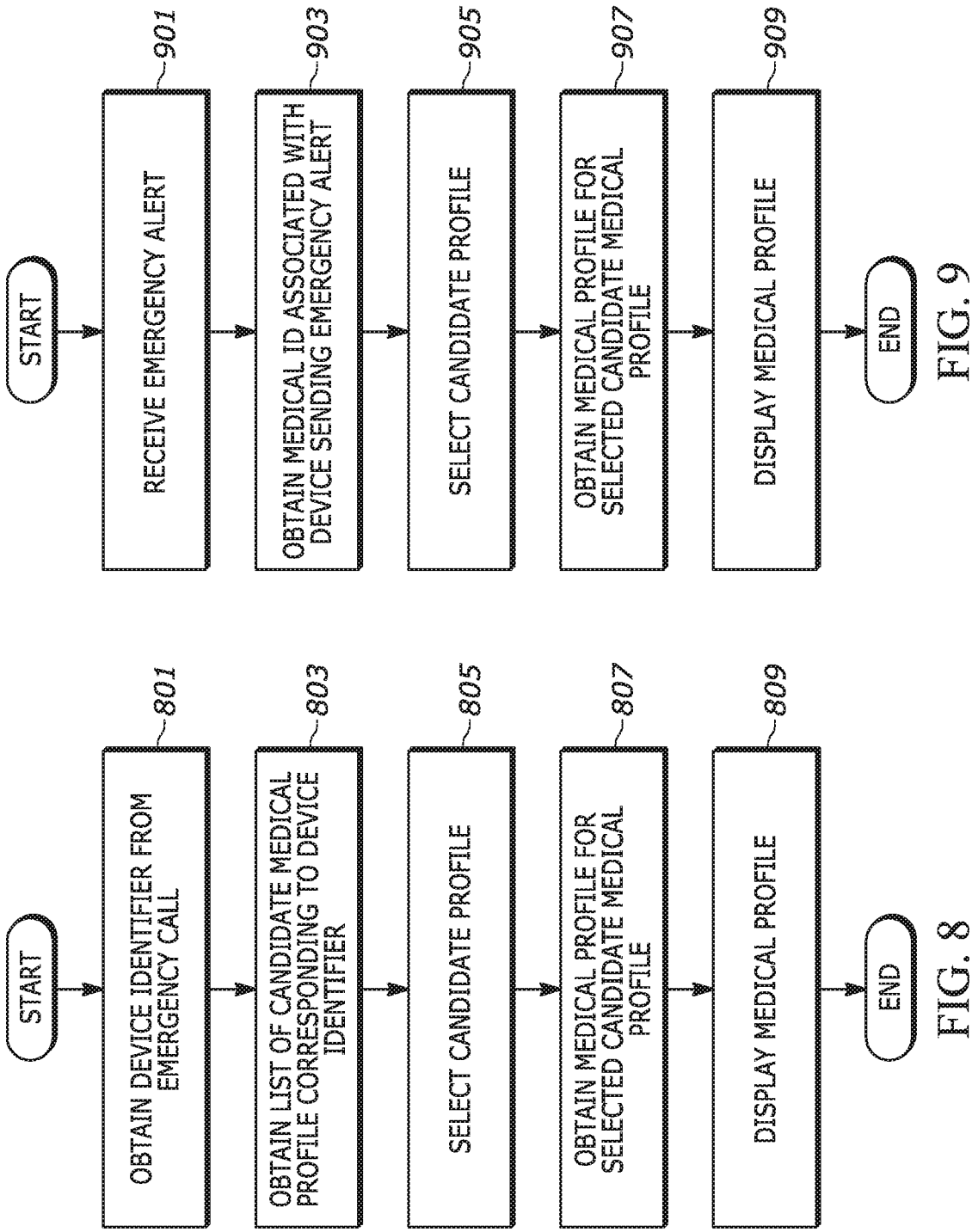

| | TELECOMMUNICATORS | EMTs |
|---|---|---|
| "DO NOT RESUSCITATE" | WANT TO KNOW THIS FIRST ABOVE EVERYTHING ELSE | WANT TO KNOW THIS FIRST ABOVE EVERYTHING ELSE |
| IMPLANTED DEFIBRILLATOR | EXTREMELY IMPORTANT TO KNOW | EXTREMELY IMPORTANT TO KNOW |
| PACEMAKERS | EXTREMELY IMPORTANT TO KNOW | EXTREMELY IMPORTANT TO KNOW |
| MEMORY IMPAIRMENT | EXTREMELY IMPORTANT TO KNOW | EXTREMELY IMPORTANT TO KNOW |
| SEIZURE DISORDERS | IMPORTANT | IMPORTANT |
| MEDICATIONS | HELPFUL WHEN GIVING OUT EMD INSTRUCTIONS SUCH AS ASA PROTOCOLS AND RESCUE MEDS | HELPFUL |
| ALLERGIES | NOT IMPORTANT UNLESS ITS AN ALLERGIC REACTION OR CHEST PAIN CALL<br><br>NOTE:<br>ASPIRIN (ASA) ALLERGY SHOULD BE A RED FLAG | EXTREMELY IMPORTANT TO KNOW (ESPECIALLY IF CALLER IS UNCONSCIOUS) |
| MEDICAL HISTORY | HELPFUL | HELPFUL |

FIG. 14

APPARATUS AND METHOD FOR EMERGENCY RESPONSE DATA ACQUISITION AND RETRIEVAL

CROSS-REFERENCE TO RELATED APPLICATIONS

The present application claims priority to U.S. Provisional Patent Application No. 62/923,093, filed Oct. 18, 2019, entitled "APPARATUS AND METHOD FOR EMERGENCY RESPONSE DATA ACQUISITION AND RETRIEVAL" which is hereby incorporated by reference herein in its entirety, and further claims priority to U.S. Provisional Patent Application No. 62/804,131, filed Feb. 11, 2019, entitled "THIRD PARTY DATA AND MEDICAL DATA FOR EMERGENCY RESPONSE," both of which are assigned to the same assignee as the present application, and both of which are hereby incorporated by reference herein in their entirety.

FIELD OF THE DISCLOSURE

The present disclosure relates generally to emergency calls, enhanced 9-1-1 (E911) and next generation 9-1-1 (NG911) emergency networks, and more particularly, to acquisition of data such as medical data for use in responding to emergencies.

BACKGROUND

Emergency networks which may also be referred to as emergency dispatch centers (EDC) including public safety answering points (PSAPs), utilize various enhanced 9-1-1 (E911) or next generation 9-1-1 (NG911) emergency network infrastructures which provide interconnection to the Internet protocol (IP) domain.

An emergency network refers to an entity that may receive an emergency call or an emergency alert and coordinate emergency assistance. An emergency network may be owned and operated by a public organization run by a municipality, county or city, or by a private organization such as a corporation or college campus. Emergency assistance provided can include medical, caregivers, firefighting, police, military, paramilitary, border patrol, lifeguard, security services, or any combination thereof. These personnel may be referred to as "Emergency Service Providers" (ESPs) or "emergency responders," or "responders." ESPs or responders could often benefit from having as much information as possible at the location of an emergency situation.

BRIEF DESCRIPTION OF THE DRAWINGS

FIG. 8 is a flowchart showing a method of operation of an emergency data manager in accordance with various embodiments.

FIG. 9 is a flowchart showing a method of operation of an emergency data manager in accordance with various embodiments.

FIG. 14 is a table with example levels of importance that emergency network personal and responders may attribute to various pieces of medical data.

DETAILED DESCRIPTION

Figure 1:
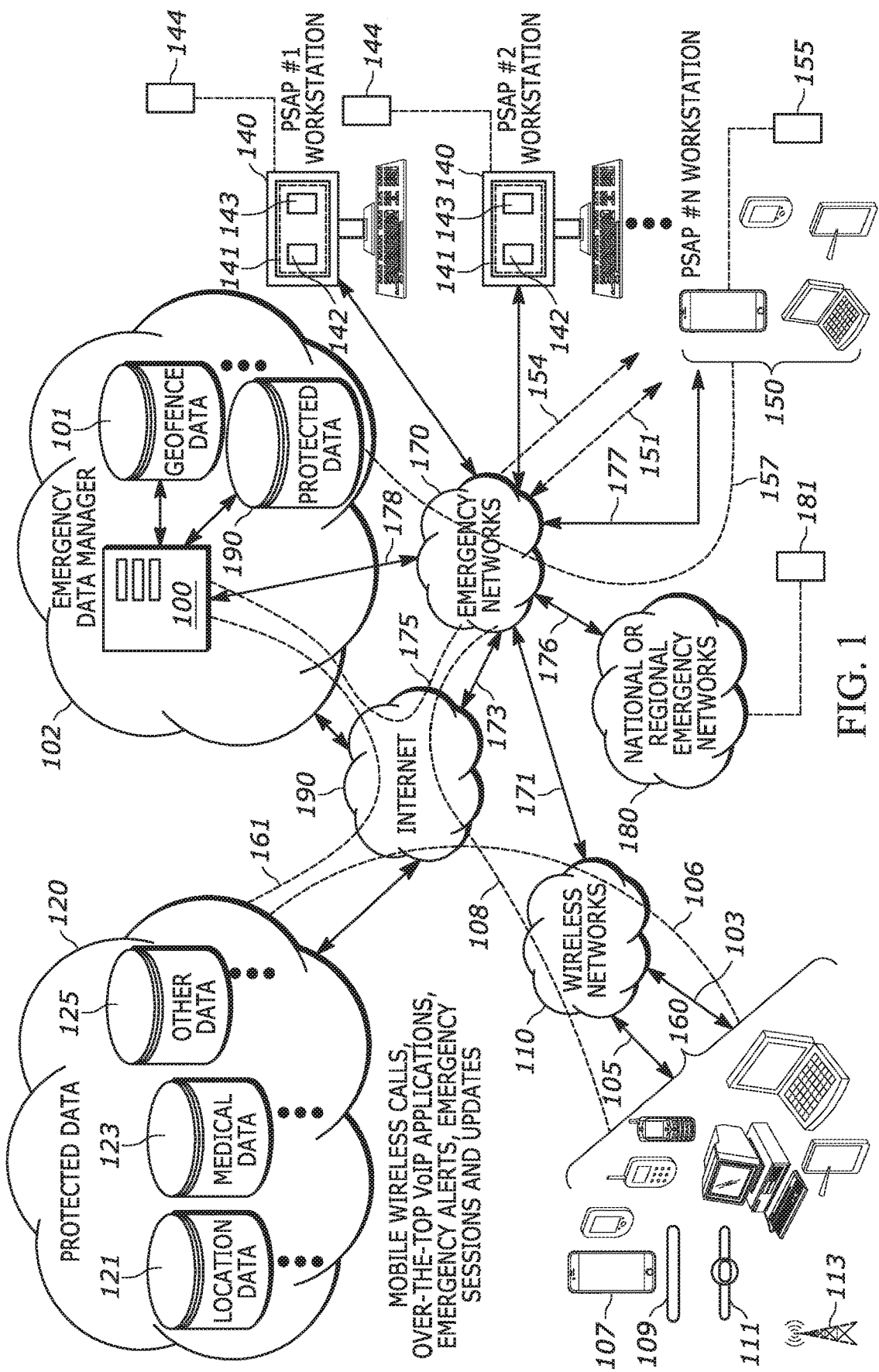
FIG. 1 is a diagram illustrating an emergency data management network in communication with various emergency networks and national or regional emergency networks.

In many emergency scenarios, a rapid response significantly increases the likelihood of a successful outcome. For example, rapidly providing certain treatment (e.g., CPR, insulin, etc.) to users undergoing an emergency can increase their likelihood of survival and reduce associated risks. Databases provided by various service providers may store critical medical data in relation to various identifiers associated with a patient. The present disclosure provides apparatuses and methods that enable such service provider information to be accessed such that the information may be used in making time-sensitive decisions which can be life-saving decisions.

Briefly, the present disclosure provides apparatuses and methods for acquisition and retrieval of emergency data such as, but not limited to, medical data and other protected data, such that the data can be provided to emergency responders during an emergency situation, while providing protection measures to preserve privacy and security of protected data. Protected data is shown to be available in an anonymized form until specifically requested and is not provided until authorization credentials are verified.

One disclosed method provides receiving an emergency data request that includes a patient identifier; retrieving protected data from a database corresponding to the patient identifier; and displaying the protected data on a display of an emergency responder device in response to the emergency data request. Retrieving protected data from the database corresponding to the patient identifier may include retrieving protected data that includes one or more anonymized candidate profiles corresponding to the patient identifier. The anonymized candidate profiles provide anonymized patient information without exposing protected data related to the patient.

The method may retrieve protected data from the database corresponding to the patient identifier by retrieving protected data that includes one or more anonymized candidate profiles corresponding to the patient identifier without retrieving personally identifiable information, and where the anonymized candidate profiles provide anonymized patient information without exposing protected data including the personally identifiable information related to the patient.

The method may further include displaying the anonymized candidate profiles on a display of an emergency responder device in response to the emergency data request; receiving a selection input corresponding to a selected one of the anonymized candidate profiles; and displaying non-anonymized medical data corresponding to the selected one of the anonymized candidate profiles on the display of the emergency responder device in response to the selection input. The method may further include: retrieving and transmitting the non-anonymized medical data in compliance with requirements for protection of personally identifiable information (PII) and protected health information (PHI). The method may further include: receiving the patient identifier from a device of a bystander caller. The method may further include: receiving the emergency data request from a responder device, where the emergency data request has emergency responder credentials; and providing limited access to the protected data by the responder device based on data access limitations specified in the emergency responder credentials. The method may further include: receiving the emergency data request from an emergency network entity on behalf of a responder device, where the emergency data request has emergency responder credentials; and providing limited access to the protected data by the responder device based on data access limitations specified in the emergency responder credentials.

A disclosed emergency data manager includes a network component, operative to provide Internet Protocol (IP) connections to a plurality of emergency network entities and to a plurality of emergency data servers and databases; and at least one processor, operatively coupled to the network component. The at least one processor is operative to: receive an emergency data request with a patient identifier; retrieve protected data from a database corresponding to the patient identifier; and display the protected data on a display of an emergency responder device in response to the emergency data request.

The emergency data manager processor may be further operative to: retrieve protected data that includes one or more anonymized candidate profiles corresponding to the patient identifier, where the anonymized candidate profiles provide anonymized patient information without exposing protected data related to the patient. The emergency data manager processor may be further operative to: retrieve protected data from the database corresponding to the patient identifier by: retrieving protected data that includes one or more anonymized candidate profiles corresponding to the patient identifier without retrieving personally identifiable information, where the anonymized candidate profiles provide anonymized patient information without exposing protected data including the personally identifiable information related to the patient.

The emergency data manager processor may be further operative to: display the anonymized candidate profiles on a display of an emergency responder device in response to the emergency data request; receive a selection input corresponding to a selected one of the anonymized candidate profiles; and display non-anonymized medical data corresponding to the selected one of the anonymized candidate profiles on the display of the emergency responder device in response to the selection input. The emergency data manager processor may be further operative to: retrieve and transmit the non-anonymized medical data in compliance with requirements for protection of personally identifiable information (PII) and protected health information (PHI). The emergency data manager processor may be further operative to: receive the patient identifier from a device of a bystander caller. The emergency data manager processor may be further operative to: receive the emergency data request from a responder device with the emergency responder credentials; and provide limited access to the protected data by the responder device based on data access limitations specified in the emergency responder credentials. The emergency data manager processor may be further operative to: receive the emergency data request from an emergency network entity on behalf of a responder device, with the emergency responder credentials; and provide limited access to the protected data by the responder device based on data access limitations specified in the emergency responder credentials.

Another disclosed method includes: pushing a plurality of anonymized candidate profiles associated with a device identifier to an emergency network entity, in response to initiation of an emergency session by a device having the device identifier, the anonymized candidate profiles providing anonymized patient information without exposing protected data related to a patient and corresponding to a non-anonymized medical profile for the patient; receiving a request from the emergency network entity for a specific non-anonymized medical profile corresponding to one of the plurality of anonymized candidate profiles; and providing a non-anonymized medical data profile corresponding to the specific anonymized candidate profile to the emergency network entity in response to the request.

Another disclosed emergency data manager includes a network component, operative to provide Internet Protocol (IP) connections to a plurality of emergency network entities and to a plurality of emergency data servers and databases; and at least one processor, operatively coupled to the network component. The at least one processor is operative to: push a plurality of anonymized candidate profiles associated with a device identifier to an emergency network entity, in response to initiation of an emergency session by a device having the device identifier, the anonymized candidate profiles providing anonymized patient information without exposing protected data related to the patient and corresponding to a non-anonymized medical profile for the patient; receive a request from the emergency network entity for a specific non-anonymized medical profile corresponding to one of the plurality of anonymized candidate profiles; and provide a non-anonymized medical data profile corresponding to the specific anonymized candidate profile to the emergency network entity in response to the request.

Another disclosed method provides pushing a plurality of anonymized protected data profiles to an emergency network in response to initiation of emergency sessions with the emergency network by a plurality of devices, where each device has a device identifier and each anonymized protected data profile is associated with a device identifier. Each anonymized protected data profile provides anonymized information without exposing protected data related to users associated with the plurality of devices and corresponds to a non-anonymized protected data profile for a patient. The method proceeds with receiving requests from the emergency network for specific non-anonymized protected data profiles, with each specific non-anonymized protected data profile corresponding to one of the plurality of anonymized protected data profiles; and providing the specific non-anonymized protected data profiles to emergency responder devices of the emergency network based on the requests.

The method may further include receiving authorization credentials for a plurality of emergency responder devices, where the authorization credentials specify protected data categories and access levels for each emergency responder device; and providing limited access to the specific non-anonymized protected data profiles to emergency responder devices based on the authorization credentials.

Turning now to the drawings wherein like numerals represent like components, FIG. 1 illustrates an emergency data manager 100 which is operative to communicate with various emergency networks 170 including, but not limited to, multiple Enhanced 9-1-1 (E911) or Next Generation 9-1-1 (NG911) emergency networks 170, via network connections 175. E911 and NG911 emergency networks are defined according to the National Emergency Number Association (NENA) standards which define applicable network architectures and protocols for communication between various network entities within the network architectures. Emergency networks are owned and operated by various emergency service providers (ESPs) such as, but not limited to, municipalities, state governments, and other public safety services (PSS) as well as private emergency service providers such as corporate security, college campus security, etc. The emergency services provided are for example, police, fire department, ambulance, etc. One type of emergency network is a public safety answering point (PSAP), which may handle emergency calls for police, fire and medical emergencies. Put another way, an ESP is an organization that owns and operates an emergency network where the emergency network includes the infrastructure, network entities, communication devices and other equipment required to provide the emergency services.

In FIG. 1, double arrowed lines represent operative coupling which may be implemented as backhaul connections between network entities, or as wireless connections between network entities and devices. Curved, dotted lines in FIG. 1 represent network connections or data connections over which data may be sent and received by respective devices, network entities or by combinations of devices and network entities sending data to, and receiving data from, each other, accordingly. The network connections may be Internet connections and may further include Virtual Private Network (VPN) pathways or other secure connections. The emergency data manager 100 is operatively coupled to emergency networks 170 via operative coupling 178, which may be implemented as network connections 175 through the Internet 190. The network connections 175 may include an Internet protocol (IP) connection between each of the emergency networks 170 and the emergency data manager 100 and may be connection oriented or connectionless. For example, the network connections 175 may include IP connections which may include a TCP (Transmission Control Protocol, also referred to as Transport Control Protocol) connection, a UDP (User Datagram Protocol) connection or a combination of both such as UDP over TCP, etc., or a combination of TCP and UDP connections, etc. An IP connection may further employ one or more TCP sockets or one or more Web Socket connections. The emergency networks may have backhaul connections 173 to the Internet 190 and backhaul connections 176 to national or regional emergency networks 180. The emergency data manager 100 may operate as an interface between the emergency networks 170, databases 120 and devices 160, to provide emergency data to the emergency networks 170. The emergency data manager 100 is operative to retrieve various types of emergency data such as location data, medical data, sensor data, camera data and other data, etc., determine the appropriate emergency network 170 authorized to receive specific emergency data, and provide that specific emergency data to the authorized emergency network. The emergency data manager 100 may, under some circumstances and for certain types of emergency data, store obtained emergency data in one or more databases which may be distributed databases. Protected data may be stored in protected data database 190 that may contain data that is subject to laws, regulations or policies that define how the data is accessed and handled.

The emergency data manager 100 may communicate with, and retrieve and obtain data from, the various databases 120, any of which may contain protected data, and may also receive and store emergency data from the devices 160. The emergency data manager 100 is operative to determine the authorized emergency network using a geofence database 101 which includes boundary information for all of the emergency networks 170 and also for national or regional emergency networks 180.

The various emergency networks 170 may include various public safety answering points (PSAPs). Each emergency network such as, but not limited to a PSAP, may include an emergency dispatch center and employ a computer aided dispatch (CAD) system. Each emergency network 170 includes various network entities such as at least one workstation 140, which may be a CAD system, a call handling system or some other type of workstation, and which provides various graphical user interfaces (GUIs) on a display 141 for use by emergency network personnel. The term "emergency network entity" refers to a hardware apparatus used to access or implement an emergency network such as, but not limited to, workstations, servers, routers, switches, laptops, desktop computers, etc. An emergency network entity hardware apparatus may include software or firmware related to its emergency network function.

Each individual emergency network 170 may include an emergency call handling system which is operatively coupled to a PSTN (public switched telephone network) and various wireless networks 110 via appropriate backhaul connections 171. The various emergency networks 170 are each operative to receive emergency calls 103 from a variety of devices 160 and a variety of device types. Each individual emergency network 170 may also receive emergency alerts 105 and establish emergency sessions 108 from the various devices 160 over the Internet 190. An emergency alert 105 may be sent as, for example, short message service (SMS) messages, SMS data messages, instant messages (IM), multi-media messages (MMS), email, or other formats of messages sent as Internet Protocol (IP) messages. For example, IP based messages may be sent using TCP, UDP, SIP, HTTP, or other mechanisms, etc. Emergency sessions 108 may also be established using these same, or other, IP protocols. An emergency session 108 refers to communication over an Internet connection between any the various types of devices 160 and an emergency network, where there is communication between one of the devices 160 and a particular emergency network of the emergency networks 170. The communication may be bi-directional. One example of a bi-directional emergency session 108 is a Voice-over-IP (VoIP) call using Session Initiation Protocol (SIP). Another example is an IP call using H.323 protocol, or some other communication protocol, etc. An emergency alert 105 may be, but is not limited to, data sent from a device 160 to a given one of the emergency networks 170. Because the emergency alert 105 will contain information that identifies the specific device 160 that sent the alert, the specific emergency network that received the emergency alert 105 may be able to respond to the device 160 by sending a response or acknowledgement message, or by making a call-back if the device 160 is for example, a mobile telephone such as a smartphone 107. The information that identifies a specific device 160 is referred to herein as a "device identifier." That is, a "device identifier" refers to information allowing identification of the device or a user of the device, such as for example, a phone number associated with a user, an email address, physical address, coordinates, IMEI number, IMSI, TMSI, IP address, BSSID, SSID or MAC address.

The various types of devices 160 that may communicate with an emergency network include, but are not limited to, desktop computers, laptop computers, tablets, mobile phones, smartphones 107, smartwatches 111 (or other health and medical tracking devices), medical bracelets 109, and various wired devices which may be Internet-of-Things (IoT) devices 113 which are operative to send and receive data from a wireless network such as, but not limited to, a 5th generation mobile network (5G network). A medical bracelet 109 may be a type of IoT device and may be operative to transmit an emergency alert 105 to an emergency network. Emergency calls may also be made from landline phones connected to a PSTN and medical bracelet 109 and/or health monitoring device, such as a medical bracelet 109, may use a wireless access point connected to the PSTN to place an emergency call 103 or send emergency alert 105.

An "emergency alert" refers to a communication relating to an emergency or non-emergency situation. That is, an emergency alert may be an emergency request for assistance where the emergency alert is associated with an emergency situation. An emergency alert may include information related to a device, the device user, past and current location, or an indication of the type of emergency such as, but not limited to, police, fire, medical, CO level, traffic accident or some other information in various combinations. An emergency alert may be associated with a non-emergency situation such as a request for a tow truck after a car breaks down. In other words, a situation that requires assistance, but is not necessarily a life-or-death critical situation. Emergency alerts may be associated with a device that sent the alert, or may be associated with a device not sending the alert such as a device making a proxy request on behalf of a second device or a member device in a group of devices, etc. An emergency alert may be "associated" with a device or user when the emergency alert relates to an emergency or non-emergency situation involving the device or user. Emergency alerts may include pointers to other sources of information such as, but not limited to, medical records and health data for the device user, or for another device user in a proxy situation, etc.

In one example of operation, an emergency alert 105 may be triggered by a device 160 in any of various ways such as, but not limited to, device fall detection, by the user pressing a soft button or a physical button (i.e. a "panic button"), a voice command, a gesture, or autonomously based on other sensor data such as via a smoke, carbon-monoxide, burglar alarm, or some other alarm, etc. In some situations, the user may confirm the emergency or provide authorization for sending the emergency alert 105.

Emergency data, such as enhanced location data, medical data, or other data, may be sent by the devices 160 to the various databases 120 and pushed to the emergency data manager 100 as part of the emergency alert 105. The emergency data may be sent from the devices 160 as updates 106 to a specific database of the various databases 120. The data updates 106 may be pushed to the emergency data manager 100 based on a subscription of a particular device 160 to the emergency data manager 100 services, or when a device 160 initiates an emergency session 108. In either case, the emergency data manager 100 may store the data in the protected data database 190 for a period of time in anticipation of an emergency data request from one of the emergency networks 170. The emergency data manager 100 is operative to provide emergency data in the protected data database 190, or access and provide emergency data in the databases 120 in response to an emergency data request. An emergency network 170 or an emergency responder device 150 may send an emergency data request to the emergency data manager 100.

Each of the devices 160 may be operative to send data updates 106 from time-to-time, or based on a schedule, to various databases 120 and this data may subsequently be used as information included in emergency alerts 105. The databases 120 may contain protected data in that the data is subject to various statutorily defined protections, such as, but not limited to, HIPAA, GDPR, or other statutorily defined data protection and data privacy requirements. The databases 120 may include location databases 121, medical databases 123 and other databases 125 with various personally identifiable data related to device 160 users. The data contained in the databases 120 is referred to as "emergency data" in that it may be retrieved by the emergency data manager 100, via an IP connection 161, in response to a detected emergency detected by the emergency data manager 100 or in response to an emergency data request.

Each emergency network 170 has at least one workstation 140 that includes one or more processors that are operative to execute one or more emergency services related applications. At least one workstation 140 also includes emergency response logic 144 in accordance with the various embodiments. In some embodiments, the emergency response logic 144 may be implemented as an application executed by the one or more processors of the workstation 140. The emergency response logic 144 is operative to provide a graphical user interface (GUI) 143 on the workstation display 141. During operation, the workstation 140 may also display other GUIs such as GUI 142, which may be related to, and provided by, other emergency response applications such as, but not limited to, an emergency call handling application or a computer aided dispatch (CAD) application.

The emergency response logic 144 is operative to communicate with the emergency data manager 100. The emergency data manager 100 may be included within an emergency data management network 102 which may include one or more servers, and one or more databases such as geofence database 101 and protected data database 190. The emergency data manager 100 may be implemented as a server having at least one processor, or may be implemented as a distributed system with multiple servers, processors, memory and databases, and may further provide cloud-based, software-as-a-service (SaaS) features and functions and/or may be implemented as SaaS using a platform-as-a-service (PaaS).

The GUI 143, in conjunction with the emergency response logic 144, are operative to retrieve and display emergency data provided by the emergency data manager 100. More particularly, the GUI 143 provides communication between an emergency network entity such as the workstation 140, and the emergency data manager 100. The GUI 143 may be implemented as a web browser interface, such as a cloud-based application interface (i.e. a software-as-a-service SaaS interface), or via a web browser plug-in, or may be associated with an application running as executable instructions, executed by one or more processors on the workstation 140, or by any other software implementation mechanism. Emergency services personnel may receive appropriate emergency services information and view emergency data via the GUI 143.

Depending on the specific operations of the emergency network and the particular type of workstation 140 software, the GUI 142 may be used by emergency services personnel to place dispatch calls to emergency responders, who receive the dispatch calls and emergency data on various emergency responder devices 150 accordingly. Emergency responders, also referred to as emergency service providers (ESPs) may utilize a variety of emergency responder devices 150 which may include, but are not limited to, desktop computers, laptop computers, tablets, mobile phones, smartphones, radios (i.e. walkie-talkies), in-vehicle computers, etc., all of which are operative to display emergency data to the emergency responders. The devices 150 may be operative to send emergency data requests 151 to a respective emergency network 170 and also authentication data 153. The devices 150 communicate with the emergency networks 170 over a combination of wireless networks 110 and proprietary wireless networks that provide wireless communications links 177. Each of the devices 150 may include a mobile emergency data application, that provides a GUI 155 and that is operative to communicate with the emergency response logic 144 and the emergency data manager 100. In response to emergency data requests 151, the emergency data manager 100 is operative to provide limited access to emergency data 157 to the emergency responder devices 150 based on the authorization level of the specific emergency responder device 150 and associated user.

An emergency data request 151 from an emergency responder device 150, may be sent either by a responder device 150, or by an appropriate one of the emergency networks 170, to the emergency data manager 100 such that the emergency data manager 100 may identify the emergency and any emergency data pertaining to the emergency stored by the emergency data manager 100 or contained within the various databases 120. In response, the emergency data manager 100, may check authorization, and then proceed to send the pertinent emergency data 157 to the requesting emergency responder device 150. In other words, in some implementations, the emergency data manager 100 may serve as a data pipeline for emergency responder devices 150 through which the emergency responder devices 150 may request and retrieve reliable emergency data through secure pathways using defined protocols and formats. The emergency data may be, but is not limited to: accurate location data, that is critical for responding to an emergency, medical data, sensor data, or other data, etc. The emergency data manager 100 is operative to obtain emergency data from various sources including other servers, databases 120, and devices 160 including sensors.

In one example of operation, an emergency alert 105 may be triggered by a device 160 in any of various ways such as, but not limited to, device fall detection, by the user pressing a soft button or a physical button (i.e. a "panic button"), a voice command, a gesture, or autonomously based on other sensor data such as via a smoke, carbon-monoxide, burglar alarm, or some other alarm, motion detector, camera, etc. In some situations, the user may confirm the emergency or provide authorization for sending the emergency alert 105.

Emergency data, such as enhanced location data, medical data, or other data, may be sent by a device 160 to an appropriate one of the emergency networks 170 as part of an emergency alert 105, or may be sent as data updates 106 to a specific database of the various databases 120. In some implementations, and/or for certain types of emergency data, the emergency data manager 100 may push emergency data to a given emergency network 170 as that emergency data is obtained by the emergency data manager 100. An emergency network 170 may also, at any time, send an emergency data request to the emergency data manager 100 such that the emergency data manager 100 may search or query the various databases 120. In some implementations, an emergency data search may be performed by the emergency data manager 100, using the IP connections 161 to the various databases 120, in response to an emergency alert 105, emergency call 103, or emergency session 108 between a device 160 and one of the emergency networks 170. In one example, the emergency data manager 100 is operative to receive Android™ Emergency Location Service (ELS) data upon initiation of an emergency call 103, emergency alert 105, or emergency session 108 established by a device 160 that utilizes the Android™ operating system. Upon receipt of ELS data, the emergency data manager 100 is operative to push the ELS data to the appropriate emergency network 170 based on a geofence analysis using the geofence database 101. The emergency data manager 100 may also perform a search of the various databases 120 using a device identifier in the ELS data to identify additional related emergency data and push that emergency data to the appropriate emergency network 170.

The emergency data manager 100 or the emergency network 170 may format stored emergency data or any received emergency data into a format that is compatible with industry standards for storing and sharing emergency data. For example, the emergency data may be formatted to be compatible with National Emergency Number Association (NENA) standards. Where emergency data is stored by the emergency data manager 100, emergency data requests may be sent to the emergency data manager 100 by an emergency network, such as via an HTTP GET request. For example, protected data may be stored in the protected data database 190 pending receipt of appropriate authorization credential by the emergency data manager 100. In other words, some emergency data may be pushed to emergency networks 170 upon receipt by the emergency data manager 100, while other data, if subject to the categorization of protected data, may only be sent upon receipt of proper authorization and/or in conjunction with an authorized emergency data request.

Emergency data requests 151, whether sent directly by a responder device 150 or via an emergency network 170 may utilize Location Information Server (LIS) protocol. For emergency data related to location, the data may include, but is not limited to, device generated location data (such as device 160 GPS chipset data), location information such as Location-by-Reference, Location-by-Value, etc. from, for example a, Location Information Server (LIS) or from other sources. Such location data that contains multiple location determination method data is referred to as hybrid location data.

Each of the emergency networks 170 may be operatively coupled, via appropriate backhaul connections 176, to one or more national or regional emergency networks 180. The national or regional networks 180 each include an emergency event application 181 which is operative to, among other things, display emergency events for a hierarchical view of emergencies being handled by one or more of the emergency networks 170.

Figure 2:
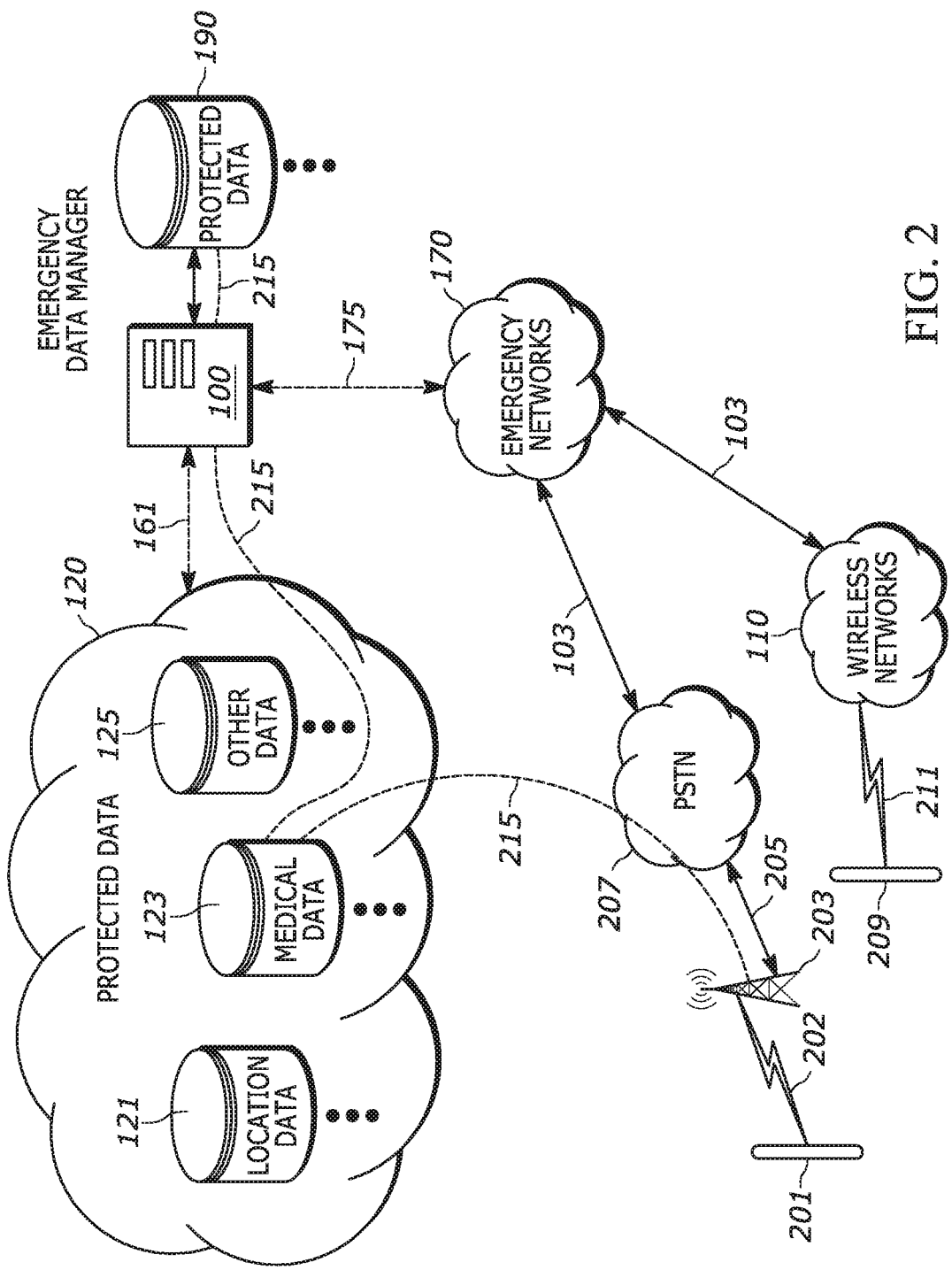
FIG. 2 is a block diagram of medical bracelets or tags that may communicate and send emergency alerts or initiate emergency calls to an emergency network.

FIG. 2 illustrates example types of medical bracelets or tags that may send emergency alerts 105 or initiate emergency calls 103. Both medical bracelet 201 and medical bracelet 209 may incorporate features such as "fall detection" in which the medical bracelet will initiate an emergency call or send an emergency alert if it detects that the patient wearing the medical bracelet has fallen. Each medical bracelet is also operative to send data updates to the databases 120, such as medical data updates 215 to the medical database 123. One type of medical bracelet 201 communicates wirelessly within a short-range area wireless link 202, such as within a home, to a receiver station 203 that has a connection 205 to a Public Switched Telephone Network (PSTN) 207. If the medical bracelet 201 detects an emergency situation, the receiver station 203 initiates an emergency call 103 to an emergency network 170. A second type of medical bracelet 209 communicates via its own wireless link 211 directly to a wireless network 110. If the medical bracelet 209 detects an emergency situation, it initiates an emergency call 103 to an emergency network 170 via a wireless network 110. The medical bracelets may also send an emergency alert to an emergency network 170 which may also be done using a wireless network 110, via the PSTN 207 or via an Internet connection in which a data session is established with an emergency network 170. The medical bracelet 201 and medical bracelet 209 are examples only, and various other types of medical bracelets and medical tags may operate differently to initiate emergency calls or send emergency alerts to emergency networks 170.

In some embodiments, medical data updates 215 are pushed to the emergency data manager 100 over an IP connection, and stored in protected data database 190. When an emergency occurs, the emergency data manager 100 may push anonymized medical data profiles, which are based on the medical data updates 215, to an appropriated emergency network 170 based on geofence analysis using geofence database 101. The emergency data manager 100 may maintain IP connections 175 with multiple emergency networks 170, where each of the IP connections 175 may include one or more Websocket connections.

Other devices and various sensors may also send emergency alerts 105 such as, but not limited to, a smart thermostat detecting a fire, a home burglar alarm system, etc. Returning to FIG. 1, when an emergency alert 105 is generated for an emergency by any of the devices 160, the emergency data manager 100 receives the emergency alert 105 and may receive a push of some associated emergency data associated with the emergency alert 105. The emergency data manager 100 also gathers other emergency data associated with the emergency alert 105, determines a nature of the emergency, determines a severity index for the emergency based at least in part on the emergency data 157, may generate a dispatch recommendation for the emergency based at least in part on the nature of the emergency and the severity index, and transmits the dispatch recommendation to an emergency network 170.

For example, the Internet-of-Things (IoT) device 113 may be a sensor device that is operative to automatically generate an emergency alert 105 in response to detecting an emergency based on sensor data gathered by the sensor device, and to push that data to the emergency data manager 100. The devices 160 may also include an intelligent vehicle system that is operative to automatically generate an emergency alert 105 in response to detecting an emergency based on sensor data gathered by the intelligent vehicle system, and push that data to the emergency data manager 100.

In FIG. 1, upon receipt of an emergency call 103 or an emergency alert 105 by an emergency network 170, an authorized call-taker or dispatch operator who has access to the emergency response logic 144 on a workstation 140 or on some other computer system, may access emergency data related to the emergency call 103 or emergency alert 105. The call-taker or dispatch operator may log in by navigating the GUI 143 and submitting their login information. When an emergency call 103 is made from one of the devices 160 to an emergency network 170, a call-taker answers the emergency call and begins to respond to the emergency. The call-taker may forward information from the emergency call to a dispatch operator. The dispatch operator may receive a push of some emergency data from the emergency data manager 100. Alternatively, or in addition to any emergency data received via a push operation, the dispatch operator may prompt the emergency response logic 144 to generate an emergency data request by submitting an identifier of a specific device 160 such as, but not limited to, a phone number or some other device identifier such as a MAC address using the GUI 143. For example, emergency network staff may submit a device identifier by copying and pasting the device identifier or typing the device identifier into an entry field of GUI 143 and selecting a search button. In that case, the emergency response logic 144 will communicate with the emergency data manager 100 to retrieve and provide any associated emergency data. However, the emergency response logic 144 can automatically retrieve the device identifier from a call-handing or dispatch application installed at the emergency network 170, and automatically generate an emergency data request without requiring input from the emergency network staff.

Figure 3:
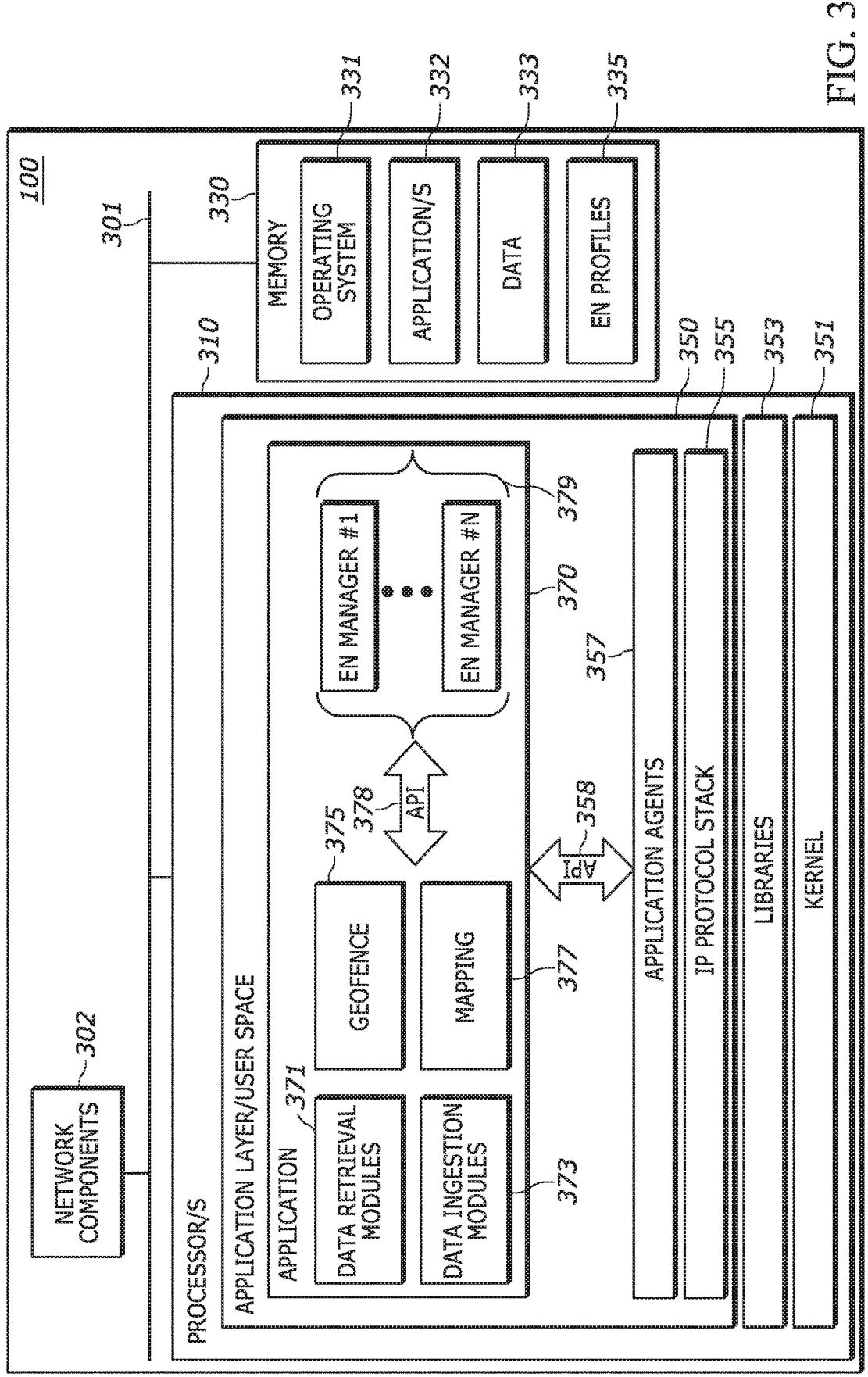
FIG. 3 is a diagram providing further details of an emergency data manager in accordance with one embodiment.

FIG. 3 provides an example implementation of the emergency data manager 100 which is an apparatus shown in FIG. 1 and FIG. 2. The emergency data manager 100 includes network components 302, at least one processor 310, and at least one non-volatile, non-transitory memory 330 in addition to RAM (random access memory). The at least one processor 310 is an emergency data management processor and is another type of apparatus disclosed herein. The network components 302 may include one or more network transceivers for Ethernet connectivity to other network entities and an Internet connection. The memory 330 stores executable instructions and data such as executable instructions for an operating system 331 and various applications 332. The memory 330 also stores data 333 which may provide a location and geofence data cache, other data caches and other data, etc. The executable instructions may be executed by the at least one processor 310.

The processor 310 may be implemented as one or more microprocessors, ASICs, FPGAs, microcomputers, microcontrollers, digital signal processors, central processing units, state machines, logic circuitries, and/or devices that manipulate signals based on operational instructions. Among other capabilities, the processor 310 is configured and operative to fetch and execute computer-readable instructions (i.e. executable instructions) stored in the memory 330. For example, the operating system 331 executable instructions, when executed by the at least one processor 310, may provide a kernel 351, libraries 353 (i.e.

application programming interfaces or "APIs"), an application layer 350 or "user space" within which the various applications are executed, and an IP protocol stack 355. The applications 332 executable instructions, when executed by the at least one processor 310, also provide data retrieval modules 371, data ingestion modules 373, a geofence module 375, a mapping module 377, and one or more emergency network managers 379. Emergency network profiles 335, stored in memory 330, may be accessed by the various modules and the emergency network managers 379 to access information needed to communicate with various emergency networks. The emergency network managers 379 communicate with the other modules of application 370 via a set of APIs 378. The processor 310 may further execute a set of application agents 357 which facilitate communication between the IP protocol stack 355 and the application 370 via various APIs 358. The application agents 357 are operative to, among other things, provide API communication between the various applications 332 and the kernel 351.

The emergency data manager 100 may be implemented as a cloud server. The term "cloud server" as used herein, refers to a server, accessible by an Internet connection, that is operative to host one or more applications that may be accessed by a computing device using a Web browser or an application resident on the computing device. The emergency data manager 100 is operative to provide a cloud-based application such as a software-as-a-service (SaaS) accessible remotely using a computer or workstation connected to the Internet and operatively coupled to the emergency data manager 100. The emergency data manager 100 may be implemented as SaaS software executed using a platform-as-a-service (PaaS) that enables development and execution of cloud-based applications.

All of the components of the emergency data manager 100 are operatively coupled by an internal communication bus 301. As used herein, components may be "operatively coupled" when information can be sent between two such components, even though there may be one or more intermediate or intervening components between, or along the connection path. Therefore, any of the various components with the emergency data manager 100, and in other example network entities and devices described herein, may be understood herein to be operatively coupled to each other where appropriate, and to be executing on one or more processors that are further operatively coupled to a memory that stores executable instructions (also referred to as "software code" or "code") for implementing the various components. Operative coupling may also exist between engines, system interfaces or components implemented as software or firmware executing on a processor and such "software coupling" may be implemented using libraries (i.e. application programming interfaces (APIs)) or other software interfacing techniques as appropriate. Such libraries or APIs provide operative coupling between various software implemented components of FIG. 3. A "module" as used herein may be a software component. That is, the data retrieval modules 371, data ingestion modules 373, a geofence module 375, a mapping module 377, and one or more emergency network managers 379 are all operatively coupled to each other via APIs 378 and are operatively coupled to the IP protocol stack 355 and to the application agents 357 via APIs 358.

All of the components and modules described herein may be implemented as software or firmware (or as a combination of software and firmware) executing on one or more processors, and may also include, or may be implemented independently, using hardware such as, but not limited to, ASICs (application specific integrated circuits), DSPs (digital signal processors), hardwired circuitry (logic circuitry), or combinations thereof. That is, any of the components or modules disclosed herein may be implemented using an ASIC, DSP, FPGA executable instructions executing on a processor, logic circuitry, or combinations thereof. In other words, the components and modules may be implemented as hardware, software or by combinations thereof. Therefore, each of the components and modules disclosed herein may be considered a type of apparatus that may be implemented and operate independently from the other components in the system. For example, any one of the data retrieval modules 371, data ingestion modules 373, geofence module 375, mapping module 377, or emergency network managers 379 may be implemented using an ASIC, DSP, FPGA, executable instructions executing on a processor, logic circuitry, or combinations thereof.

The various embodiments also include computer readable memory that may contain executable instructions, for execution by at least one processor, that when executed, cause the at least one processor to operate in accordance with the emergency data manager 100 and other functionality herein described. The computer readable memory may be any suitable non-volatile, non-transitory, memory such as, but not limited to, programmable chips such as EEPROMS, flash ROM (thumb drives), compact discs (CDs) digital video disks (DVDs), optical drives, etc., that may be used to load executable instructions or program code to other processing devices or electronic devices such as those that may benefit from the features and methods of operation herein described. The executable instructions may also include the various operating system environments and the kernel. For example, the memory 330, which is a non-volatile, non-transitory memory, may store executable instructions for execution by the at least one processor 310 that when executed, provide the data retrieval modules 331, data ingestion modules 373, geofence module 375, mapping module 377, or emergency network managers 379.

The emergency data manager 100 is operatively coupled to a geofence database 101 which stores jurisdictional boundary data for various emergency networks 170 as well as for the national or regional emergency networks. The geofence module 375 is operative to access the geofence database 101 and determine which emergency network 170 should receive specific emergency data obtained by the data ingestion modules 373, based on analysis of the geofences specified in the geofence database 101. The emergency data manager 100 is operative to store and retrieve emergency data from the various databases 120, and may function as an interface between emergency networks, the various databases 120 and devices 160 to receive and store emergency data. The stored emergency data can be transmitted or distributed to emergency networks and emergency responder devices 150 before, during, or after emergencies. The emergency data manager 100 is operatively coupled to a protected data database 190 which stores protected data related to emergencies. Protected data is either not stored by the emergency data manager 100 or is stored only for a predetermined period of time as defined by laws, regulations or policies, in the protected data database 190. The emergency data manager 100 may receive emergency data from any of the devices 160 and such data may include, but is not limited to, locations, medical history, personal information, or contact information. The emergency data manager 100 may receive emergency data from any of the devices 160 and such data may include, but is not limited to, locations, medical history, personal information, or contact information. The emergency network managers 379 are operative to check emergency network credentials to determine authorization and access levels to protected data stored in the protected data database 190 or in the other databases 120.

The emergency data manager 100 includes data ingestion modules 373 and data retrieval modules 371. The data ingestion modules 373 are operative to communicate with the various databases 120 to obtain emergency data and may include a location ingestion module, an additional data ingestion module, and one or more multimedia ingestion modules. The location ingestion module is an emergency location service ingestion interface which is operative to post or receive emergency locations. The location ingestion module may be a REST API that is operative to receive an HTTP POST including location data when an emergency alert 105 is generated or when an emergency call 103 is received from a device 160. The location data may include a location generated concurrently or in response to the generation of the emergency alert 105, which may initiate an emergency call 103 or emergency session for requesting emergency assistance. This generated location data may be, for example, location data from a device 160 GPS chipset, such as GPS coordinates. This data may also include data from a device 160 inertial-measurement-unit (IMU). The location data may be generated before an emergency alert 105 such as, for example, when a medical bracelet IMU detects that a patient has fallen. In another example, when an emergency call 103 is made from a device 160, the location ingestion module of the data ingestion modules 373 may receive a location recently generated by the device 160 GPS chipset, or by a device 160 triangulation algorithm, or other device 160 location mechanism, thereby ensuring that a location for the emergency is available as quickly as possible. The location data may include a device-based hybrid location generated by a device 160 which has sent an emergency alert 105. A GPS chipset within the device 160 may generate the location data. The location data may also include a location data generated by a second device 160 that is communicatively coupled to the device 160 that sent the emergency alert 105. For example, a wearable device such as a medical bracelet or smartwatch, that does not include location capabilities, may use the location services location from a mobile phone with which it is paired. The location ingestion module of the data ingestion modules 373 may communicate with a device 160 via a mobile application installed on the device 160 or via firmware or an operating system of the device 160.

The location data generated by a device 160 prior to an emergency occurrence may be accessible by an authorized one (based on device 160 location) of the emergency networks 170 during an emergency. For example, a taxi company may have software that transmits the location of its cars or assets to the emergency data manager 100, or another server, preemptively. Thus, when an emergency arises, the location of the affected taxi can be made accessible quickly to send for help. Further, location data generated by a device 160 after an emergency has commenced may be made accessible to one of the emergency networks 170 during the on-going emergency. For example, updated location data of a hijacked taxi may be periodically transmitted to the emergency data manager 100 and made accessible to one or more of the emergency networks 170.

The data ingestion modules 373 may also provide an interface for posting or receiving static or dynamic emergency profile data. Such additional data may include, but is not limited to, medical data, personal data, demographic data, and health data, which may be obtained from the various databases 120. For example, medical data may include information relating to a person's medical history, such as medications the person is currently taking, past surgeries or preexisting conditions. Personal data may include a person's name, date of birth, height, weight, occupation, addresses such as home address and work address, spoken languages, etc. Demographic data may include a person's gender, ethnicity, age, etc. Health data may include information such as a person's blood type or biometrics such as heart rate, blood pressure or temperature. Additional data may further include data received from connected devices such as vehicles, IoT devices 113, and wearable devices such as medical bracelet 109, smartwatch 111 or other devices, etc. For example, intelligent vehicle systems may generate and send data regarding a crash, such as the speed at which the vehicle was moving just before the collision, where the vehicle was struck, the number of occupants, etc. The data ingestion modules 373 may be implemented in whole or in part using a REST API, for example using JSON (JavaScript Object Notation).

In one example of operation, if an emergency call 103 is made from a mobile phone, or if an emergency alert 105 is sent, the mobile phone may receive a heart rate of the person who made the emergency call from a smartwatch 111 worn by the person and communicatively coupled to the cell phone via a Wi-Fi™ or Bluetooth™ connection or some other wireless connection. The mobile phone may therefore send the heart rate to the data ingestion modules 373, along with any other additional data, in an HTTP POST. The data ingestion modules 373 may communicate with a device 160 via a mobile application installed on the device 160 or integrated into the firmware or operating system of the device 160. Additional data may also be sent to the data ingestion modules 373 from a network server. The data ingestion modules 373 may be accessed by any connected platform that receives data that might be relevant in an emergency. Connected platforms, such as the various databases 120, may therefore send additional data to the data ingestion modules 373 at any time. A website, web application, or mobile application may communicate with the data ingestion modules 373 and may allow device 160 users to create profiles to send additional data included in the profiles to the data ingestion modules 373 every time a profile is created or updated.

The data ingestion modules 373 may also include a multimedia ingestion module to provide an interface for posting or receiving data such as audio or video streams obtained during an emergency from a device 160 that is proximal to the emergency. In one example of operation, if an emergency alert 105 is generated by an intelligent vehicle system installed in a vehicle in response to the vehicle experiencing a collision, the emergency alert 105 is sent to one of the emergency networks 170 by the intelligent vehicle system or by another device 160 communicatively coupled to the intelligent vehicle system, such as a mobile phone coupled to the intelligent vehicle system via Bluetooth™. In response to generating the emergency alert 105, the intelligent vehicle system may additionally begin streaming audio and video from microphones and cameras installed inside or outside of the vehicle to the emergency data manager 100 through the data ingestion modules 373. A mobile phone communicatively coupled to the intelligent vehicle system may additionally or alternatively stream audio or video from microphones and cameras integrated into the mobile phone to the emergency data manager 100 through the data ingestion modules 373. One or more multimedia ingestion modules of the data ingestion modules 373 may be implemented wholly or partly using REST APIs that are accessed with an HTTP POST.

After receiving the relevant data, the data ingestion modules 373 can store the data in one or more databases operatively coupled to the emergency data manager 100, such as the protected data database 190. The emergency data manager 100 may be operatively coupled to databases such as, but not limited to, a location database, the geofence database 101, the protected data database 190 etc. The emergency data manager 100 databases may also be operatively coupled to, or otherwise accessible by, one of the emergency networks 170. The data ingestion modules 373 are operative to tag or otherwise associate received data with an identifier of a user or specific device 160 associated with the data. For example, the data ingestion modules 373 may tag received data with a user ID number, an email address, or a phone number (i.e. caller ID), a MAC address, or other device or user identification information, etc. The data ingestion modules 373 may also tag received data based on the data source using, for example, a device name or type, an application name, user name, phone number, corporate account, or etc. All data received by the data ingestion modules 373 is also analyzed by the geofence module 375 to determine which emergency network 170 should receive the data.

An individual or group of individuals may be associated with multiple identifiers. In an example of operation, if the data ingestion modules 373 receive a location generated by a phone associated with the phone number +1-555-555-5555, associated with John Doe, the data ingestion modules 373 may also receive a heart rate from a smartwatch associated with the email address jobndoe@email.com, which is an identifier that is also associated with John Doe. In this example, the data ingestion modules 373 tag the location with the phone number "+1-555-555-5555," and tag the heart rate with the email address "johndoe@email.com," thereby associating both the location and the heart rate with John Doe in the emergency data manager 100 databases.

Ingestion data that enters the emergency data manager 100 may include various data fields and associated data entries within the data fields. The emergency data manager 100 maintains a list of expected data fields so that the data entries can be entered within a specific data field.

The emergency data manager 100 may include data retrieval modules 371. The data retrieval modules 371 may include a location retrieval module, an additional data retrieval module, and one or more multimedia retrieval modules. For example, a location retrieval module may provide an interface for retrieving location data from the emergency data manager 100 databases. The location retrieval module may be implemented wholly or partly via a JSON REST API that is operative to receive a query or request such as, but not limited to, an HTTP GET request, from the emergency networks 170 or an emergency responder device 150.

The data retrieval modules 371 may provide a single GET endpoint for retrieving either the latest or paginated list of locations for a specific caller ID, and/or associated protected data from the protected data database 190. For example, a phone number associated with a device 160 from which a location was received may be included in a header, body, or metadata of a request sent to the data retrieval modules 371. The emergency data manager 100 may then retrieve a location or set of locations from the emergency data manager 100 databases and deliver the location or set of locations to the relevant authorized emergency network 170 or to an emergency responder device 150 associated with the authorized emergency network. The location retrieval module of the data retrieval modules 371 may be a location information server (LIS), in which the LIS may further be a NG911 standards-based XML API for the retrieval of location data from the emergency data manager 100 databases. The location retrieval module of the data retrieval modules 371 may be operative to accept HELD requests from the emergency networks 170 or from emergency responder devices 150 and to return location data for a specific caller ID or anonymous reference.

The data retrieval modules 371 may also include an additional data retrieval module implemented as a JSON REST API for the retrieval of emergency or additional data. Additional data may include, but is not limited to, medical data, personal data, demographic data, health data or other data which may be protected data. Additional data may also include data received from connected devices 160 such as, but not limited to, vehicles, IoT devices, and wearable devices. The additional data retrieval module of the data retrieval modules 371 may be operative to receive a query or request, such as an HTTP GET request, from an emergency network 170 or emergency responder devices 150. The additional data retrieval module of the data retrieval modules 371 may then, in response to a request, retrieve additional data associated with a specific or particular identifier of a user or a device 160 associated with the user, such as a phone number, and return the data to the emergency network 170 or emergency responder device 150. The data retrieval modules 371 may further include one or more multimedia retrieval modules, which function similarly to the location retrieval module and additional data retrieval module, for the retrieval of data stored in the emergency data manager 100 databases not retrieved by the location retrieval module or additional data retrieval module such as multimedia streaming data.

The emergency data manager 100 determines which of the emergency networks 170 and associated emergency responder devices 150 have authorization to receive particular types of emergency data. The emergency network managers 379 are operative to access emergency network profiles 335 and determine access levels to emergency data for emergency network entities and personnel. For example, a given emergency network 170 or emergency responder device 150 may, in certain circumstances, be granted access only to a particular subset of emergency data. For example, a police officer may only be given access to the location emergency data, while an EMT (emergency medical technician) may only be given access to an additional data emergency data. However, a given emergency network such as a national or regional emergency network, or associated emergency responder device 150, may be given differential access to the entirety of the emergency data, or to particular emergency data categories within the databases based on any factor or set of factors. A management portal may be provided by the emergency network managers 379 to determine which emergency data categories are returned from one of the emergency networks 170 to a particular emergency network 170 or emergency responder device 150. Other data services corresponding to the various databases 120 may also be coordinated with respect to granting access to protected data.

During an emergency, the emergency data manager 100 is operative to detect the emergency and/or otherwise identify the need to provide emergency data pertaining to the emergency. In response to detecting an emergency, the emergency data manager 100 is operative to identify any emergency data pertaining to the emergency stored within the databases 120 and protected data database 190, and retrieve and transmit the pertinent emergency data to the appropriate emergency network 170. The emergency data manager 100 may act as a data pipeline that automatically pushes emergency data to emergency networks that would otherwise be without access to emergency data that is critical to most effectively and efficiently respond to an emergency. Location data stored within, and/or obtained and provided by, the emergency data manager 100, enables emergency responders to arrive at the scene of an emergency faster, and the additional emergency data stored within, and/or obtained and provided by, the emergency data manager 100 enables emergency responders to be better prepared for the emergencies they face.

The emergency data manager 100 is operative to provide a cloud-based application to multiple emergency networks 170 by establishing network connections via the IP protocol stack 355, with various emergency network entities such as a call handling workstation, CAD workstation etc. Other examples of emergency network entities include, but are not limited to, servers, desktop computers, laptops, routers, switches, etc. that are operative to send and receive data. The network connections may be transport control protocol (TCP) connections and may utilize WebSocket connections between the emergency data manager 100 and an emergency network entity. The geofence module 375 is operative to determine emergency network jurisdictional boundaries and to show the jurisdictional boundaries on a graphical user interface as a jurisdictional map view. The mapping module 377 is operative to generate the jurisdictional map view and to also post emergency data locations as location indicators on the map. For example, location indicators may show the location of incoming emergency calls that the emergency network has received, or is receiving. The emergency network managers 379 provide authentication and login capabilities for the various emergency networks and enable APIs 378 for communication between the emergency network entities and the data ingestion modules 373, data retrieval modules 371, geofence module 375, and mapping module 377.

Emergency networks 170 and their corresponding emergency network entities are associated with a given geographic boundary. Based on the geographic boundary for a respective emergency network 170, a jurisdictional map view customized for the respective emergency network 170 may be generated and provided to emergency network entities such as workstations 140 for display. Within the jurisdictional map view for a given emergency network 170, location indicators for emergencies occurring within its geographic boundary may be displayed. The jurisdictional map view for a given emergency network 170 may include one or more geofences associated with the respective emergency network 170 and surrounding areas.

The geofence module 375 is operative for managing geofence data for emergency networks 170 including assigning geofences to one or more emergency responder devices 150 or emergency network members, etc. The emergency data manager 100, via the geofence module 375, is operative to filter all incoming emergency data related to devices 160, by geofences. Emergency networks 170 utilize geofences that define jurisdictional boundaries within which a specific emergency network is authorized to respond to emergencies. For example, a city police department may have jurisdictional authority over the entire city, or of only a portion of the city. A geofence would represent the perimeter of the portion of the city that the respective police department serves. A geofence may therefore be considered a representation of a virtual perimeter overlaying a real-world geographic area.

Geofences may be used to define a county boundary, a state boundary, a collection of postal/zip codes, a collection of cell sectors, or etc. A geofence may be defined using simple shapes such as rectangle, triangle, circle, etc., or may be defined using complex polygons, etc. Geofences may also refer to approximations where the "approximated" geofence encloses an approximation of a jurisdictional boundary or some other boundary and may also include buffer regions extending outside the perimeter, for example one-mile or such beyond the primary geofence perimeter.

Some geofences can be dynamically generated by the emergency data manager 100. For example, a dynamic geofence may be generated as a radius around a point location at which an emergency is occurring. In another example, a geofence may be represent non-emergency network boundaries such as school zones or neighborhood boundaries, etc. The use of a geofence is referred to as geofencing. One example of geofencing involves a location-aware device or a location-based service (LBS) monitoring when the device enters or exits a given geofence. This means that the device is monitored within the geographic boundaries defined by the given geofence. Entry or exit from given geofence by the device may trigger an alert to the device's user as well as messaging a given network monitoring the geofence. The monitoring network may be an emergency network 170 but could be other types of networks as well. The geofence information may contain the device location, which could be sent to a mobile telephone, an email account or to some other system or network entity.

In the context of emergency services, one or more geofences may correspond to the jurisdictional boundaries of an emergency network 170. The emergency network 170 may be operated by a public entity and may be for example, a public safety answering point (PSAP), a police department, a fire department, a federal disaster management agency, national highway police, etc., which have jurisdiction over a designated area and, sometimes, overlapping areas. Geofences are used to define the jurisdictional boundaries using various Geographic Information System (GIS) formats. A GIS file format refers to one or more standards for encoding geographical information into a computer file.

For maintaining the privacy, security and integrity of emergency data, geofencing is applied to ensure that emergency data flows only the emergency network 170 having authority to access the information and responds to the given emergency. Applying geofence filters to the emergency data also allows additional avenues for monitoring, both visibility and control, over the emergency data manager 100 to detect anomalies or spikes and to reduce the risk of security breaches. The geofence module 375 monitors all accesses to emergency data, both incoming and outgoing from the emergency data manager 100 and is operative to filter emergency data to the appropriate authorized emergency network 170 or emergency responder device 150.

In an example of emergency data manager 100 operation, an emergency alert may be triggered by a given device 160, for example by fall detection, by a user pressing a soft button, a physical button, initiating a voice command, or gesture, or autonomously based on sensor data such as from a smoke alarm. In this example, the user may be prompted to confirm the emergency or otherwise provide authorization for sending the emergency alert. However, for a fall detection scenario, a confirmation would not be required because the patient may be incapacitated. Emergency data, such as an enhanced location and additional data regarding the user, such as the user's medical history, may then be delivered by the device 160 to the emergency data manager 100 and stored in a database such as protected data database 190. The emergency data manager 100 may format the emergency data into a format that is compatible with industry standards for storing and sharing emergency data. For example, the emergency data may be formatted to be compatible with National Emergency Number Association (NENA) standards. The emergency data manager 100 may then perform a push operation to push the emergency data to an authorized emergency network entity. After the push operation, the emergency data manager 100 may delete any temporarily stored data if required for compliance with privacy laws, regulations and policies. For medical data, the emergency data manager 100 may push a candidate profile that provides basic information to be used by emergency network 170 personnel to identify a patient. Once the emergency network 170 personnel select the candidate profile on their GUI 143, the protected data for which they are authorized to receive will be pushed to their workstation 140. Likewise, emergency personnel in the field may receive the protected data using an emergency data application 155 on an emergency responder device 150.

Alternatively, or in addition to push operations, emergency data may also be obtained by the emergency networks 170, such as by a PSAP responding to an emergency alert, by sending a query to the emergency data manager 100. The query may be an emergency data request using, for example, an HTTP GET request. The emergency data request may also be in the form required by the Location Information Server (LIS) protocol. In response to the emergency data request, the emergency data manager 100 sends an appropriate response including relevant emergency data to the requesting party via an encrypted pathway. The emergency data request may be in the form of an HTTP-Enabled Location Delivery (HELD) and the response from the emergency data manager 100 may be in the form of a Presence Information Data Format Location Object (PIDF-LO) as defined by the Internet Engineering Task Force (IETF).

The emergency data request includes an authorization code, also referred to as an "authorization token", in the body, header, or metadata of the request, and the emergency data manager 100 checks that the authorization code is active before providing a response to the requesting party. Authorization may be provided in the "Authorization" header of the emergency data request using HTTP Basic Authentication. For example, authorization may be a base64-encoded user name and password for an account associated with the requesting party. Emergency data requests are sent over public networks using API access keys or credentials. Transport Layer Security (TLS) may be used in the requests and responses from the emergency data manager 100 for encryption security. In some implementations, the API access keys or credentials are sent using Extensible Markup Language (XML) in a message header and may be further encrypted for additional security. If an emergency data request includes an inactive or expired credential or access key, an error response may be generated and sent to the requesting entity by the emergency data manager 100. The emergency network managers 379 are operative to verify the access keys or credentials and enable the data retrieval modules 371 to respond to verified authorized emergency data requests by sending the pertinent emergency data.

Emergency data may include locations and additional data such as protected data. Emergency data may include one or more emergency data categories, also referred to as "data categories". The emergency data categories may include, for example: service data reference, full name, email, emergency contacts, addresses, language, occupation, phone numbers, websites, gender, height, weight, ethnicity, profile picture, allergies, medical conditions, medications, disabilities, blood type, medical notes, birthday, and additional comments. Emergency data categories may be tagged with tags for specific types of data such as "demographics" or "medical data." For example, gender, height, weight, ethnicity, profile picture (image-url) may be tagged as demographic data. Medical data protected under HIPAA and other laws may be tagged as "HIPAA" or "private." Medical data may include information on one or more of allergies, medical conditions or illnesses, medications, disabilities, blood type, medical notes, and other medical information. Medical information protected under HIPAA are encrypted and/or anonymized. Some data are tagged as "general" or another similar tag, wherein access is not specifically restricted.

The emergency data manager 100 may store emergency data requested by an emergency network entity such as workstation 140 in a remote database, such as the protected data database 190, for a certain period of time after receiving the request for the emergency data regarding a user and any electronic devices 160. A purge period of time may be set as a timer value, such as a timer countdown or a set time point, which may be defined by the emergency network that sent the emergency data request. An emergency data purge period may be, for example an interval between one to forty-eight hours, or between one to twelve hours. However, a purge period may be less than one hour due to security and privacy concerns, such as between one and forty-five minutes, or any time interval from five to thirty minutes.

After a timer for an emergency data purge has expired, and if no new requests for the emergency data pertaining to the particular user and the particular electronic device 160, or other devices associated with the user, are received, the emergency data manager 100 may mark any particular related database entries for deletion and wait for another, different, time-out interval. After a particular second time-out interval has also been completed, and if no new requests for emergency data for the particular user or associated electronic devices 160 are received, then the emergency data manager 100 may remove the specific marked entries from the databases in the next cycle of database updates.

After adding the emergency data in a database such as protected data database 190, the emergency data manager 100 may proceed to keep updating the emergency data on a periodic, or as-needed basis. In other words, the data regarding a user or electronic device 160 is kept current such that the most recent and accurate emergency data can be provided to emergency responders. The emergency data manager 100 is updated with emergency data from devices 160, and/or databases 120, for all the emergency data pertaining to all users and their associated electronic devices 160. As an alternative to having a purge period defined by a timer, a purge period may be based on an on-going emergency session such as an emergency call. For session-based purging, emergency data may be deleted after the emergency session has been terminated. To further ensure that the specific emergency data is no longer required, session-based emergency data purging may be performed after a predetermined time delay following emergency session termination, such as a time delay of between one and fifty minutes. A time delay is also beneficial in the case of dropped calls, follow-up calls, etc.

In some non-emergency situations, there is a need to access location data, user data, emergency data or sensor data. For example, a user of an electronic device 160 may grant authorization to family members to access the user's location data. Accordingly, if a family member requests location data for a user, access is granted if there is proper authorization. In another example of location data access, an employee may be required to share location data with an employer, for example through a corporate operations center, such that the corporate operations center is notified when the employee is in an emergency. In another example, a taxi operations company may request and obtain location data of one or more fleet members to keep track of its vehicles, for example, via an onboard vehicle console or terminal. All of these emergency data accesses are monitored by the emergency data manager 100 and are subject to proper authentication credential before being provided.

Figure 4:
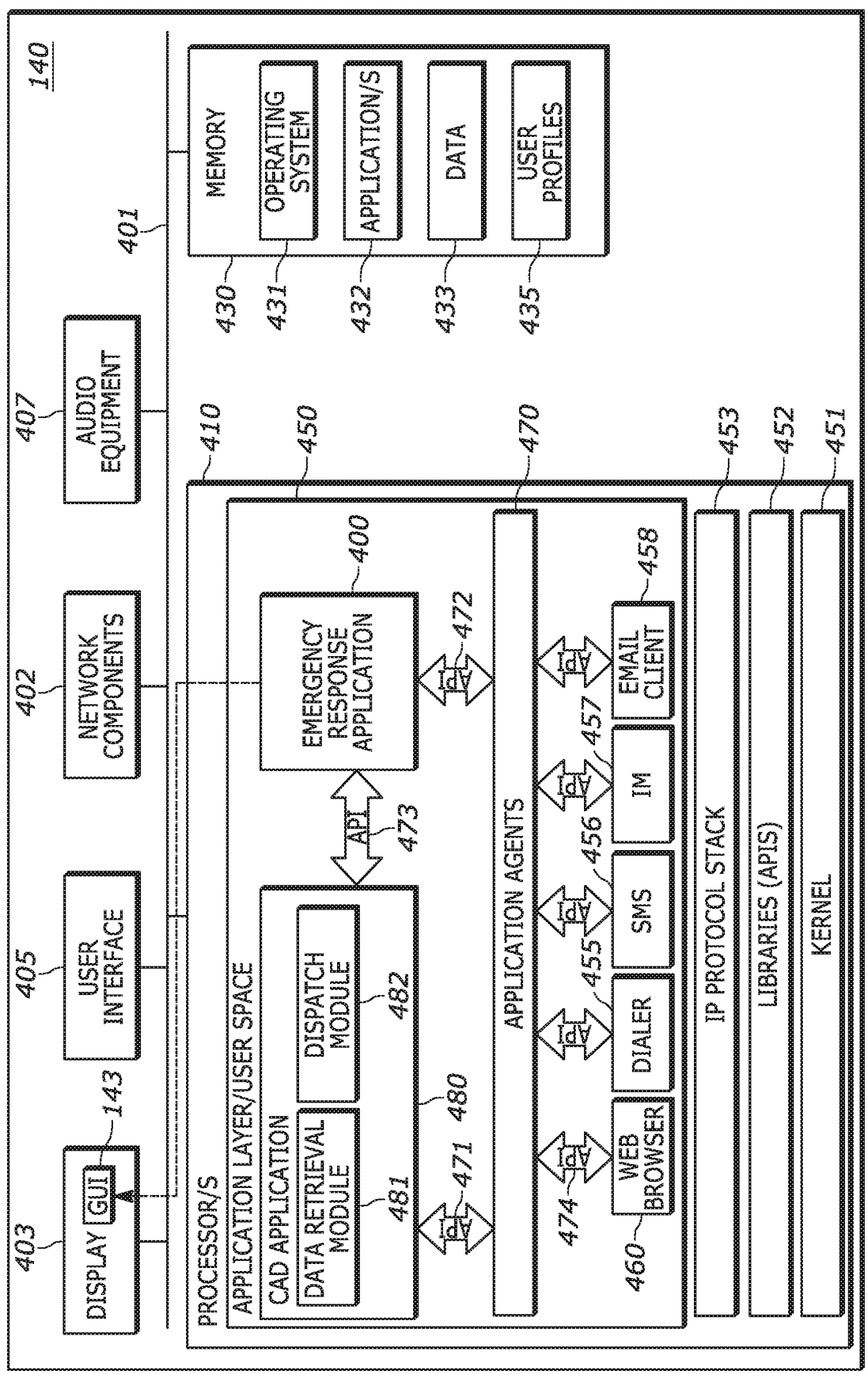
FIG. 4 is a diagram of an example emergency network entity having an emergency response application in accordance with one embodiment.

FIG. 4 provides an example CAD workstation 140 which is one example of an emergency network entity. An emergency network may be implemented with multiple emergency network entities of various kinds and therefore may have multiple workstations for example one or more call handling workstations, one or more CAD workstations, etc., in addition to routers, switches, hubs, access points, and other emergency network entities, etc. The example CAD workstation 140 may include a display 403, a user interface 405, audio equipment 407, network components 402, at least one processor 410, and at least one non-volatile, non-transitory memory 430 in addition to RAM. The network components may include one or more network transceivers for Ethernet connectivity to other workstations and devices and an Internet connection. The memory 430 stores executable instructions and data such as executable instructions for an operating system 431 and various applications 432. The memory 430 also stores data 433 which may provide data caching. User profiles 435 store emergency network personnel profiles including login credentials for authorized users of the workstation 140.

The processor 410 may be implemented as one or more microprocessors, DSPs, ASICs, FPGAs, microcomputers, microcontrollers, digital signal processors, central processing units, state machines, logic circuitries, and/or devices that manipulate signals based on operational instructions. Among other capabilities, the processor 410 is configured and operative to fetch and execute computer-readable instructions (i.e. executable instructions) stored in the memory 430. For example, the applications 432 executable instructions, when executed by the at least one processor 410, may provide an operating system, a dialer application 455, a short-message-service (SMS) application 456, an instant message (IM) application 457, a web browser 460, an email client 458 and one or more instant message (IM) and voice applications which may each provide IM and voice call capability separately or in combination. The operating system may include a kernel 451, libraries 452 (also referred to as "application programming interfaces" or APIs), an IP protocol stack 453, and an application layer 450 or user space within which the various applications are executed.

In the example workstation 140 of FIG. 4, the applications 432 executable instructions, when executed by the at least one processor 410, provide a standalone emergency response application 400 with associated GUI 143, a computer aided dispatch (CAD) application 480 including an data retrieval module 481, a dispatch module 482, and an associated GUI 142 described in FIG. 1. In the example implementation illustrated in FIG. 4, the emergency response logic 144 shown in FIG. 1 is operatively implemented as the standalone emergency response application 400 in accordance with an embodiment.

The standalone emergency response application 400 is operative to communicate with the emergency data manager 100 and to request emergency data such as medical data and other emergency data which may be protected data. The GUI 143 of the emergency response application 400 is operative to communicate with the emergency data manager 100 to send emergency data queries using a device identifier, and also to receive emergency data that is pushed to the emergency response application 400 by the emergency data manager 100.

The emergency response application 400 provides the GUI 143 on the workstation display 403, and displays augmented emergency data such as, but not limited to, augmented location data received from the emergency data manager 100. Communication is established between the emergency response application 400 and the emergency data manager 100 using the IP protocol stack 453 and a network connection is established which may be a TCP connection and which may include one or more WebSocket connections.

Figure 5:
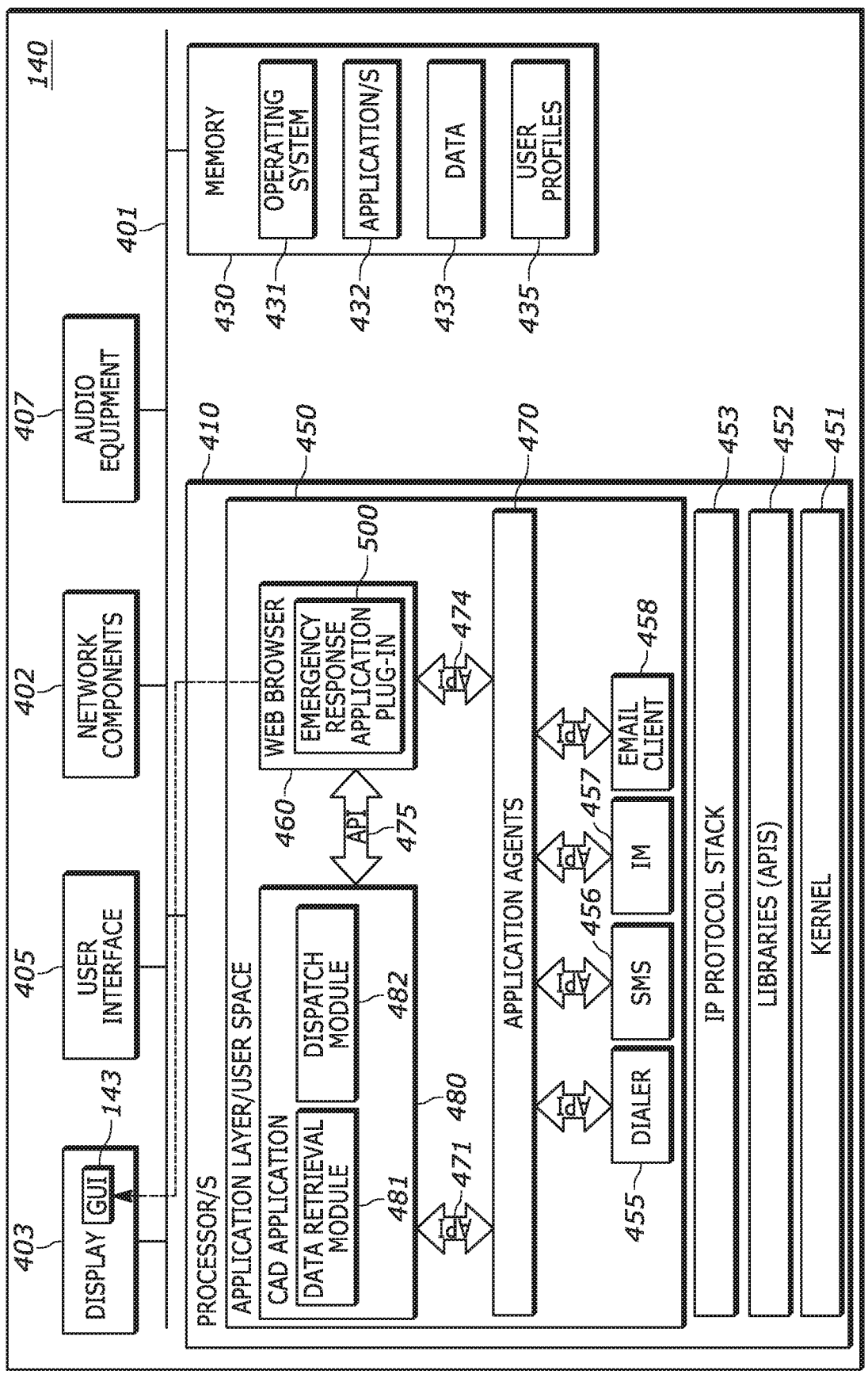
FIG. 5 is a diagram of an example emergency network entity having an emergency response application plug-in accordance with one embodiment.

FIG. 5 is a diagram illustrating another example emergency network workstation 140 having an emergency response application plug-in 500 with a Web browser 460 in accordance with another embodiment. In the example implementation of FIG. 5, the Web browser 460 communicates with the emergency data manager 100 to provide the GUI 143 as a SaaS interface. In other words, the emergency response application plug-in 500 is operative to use an established IP protocol stack 453 connection between the workstation 140 and the emergency data manager 100 using the Web browser 460. The emergency response application plug-in 500 is operative to receive pushed emergency data from the emergency data manager 100 and display the emergency data on the GUI 143. The emergency response application plug-in 500 in conjunction with the Web browser 460 also enables emergency data queries to the emergency data manager 100 to obtain emergency data, in addition to any emergency data received via a push operation. An emergency data query sent to the emergency data manager 100 by the emergency response application plug-in 500 may utilize one or more WebSocket connections.

Figure 6:
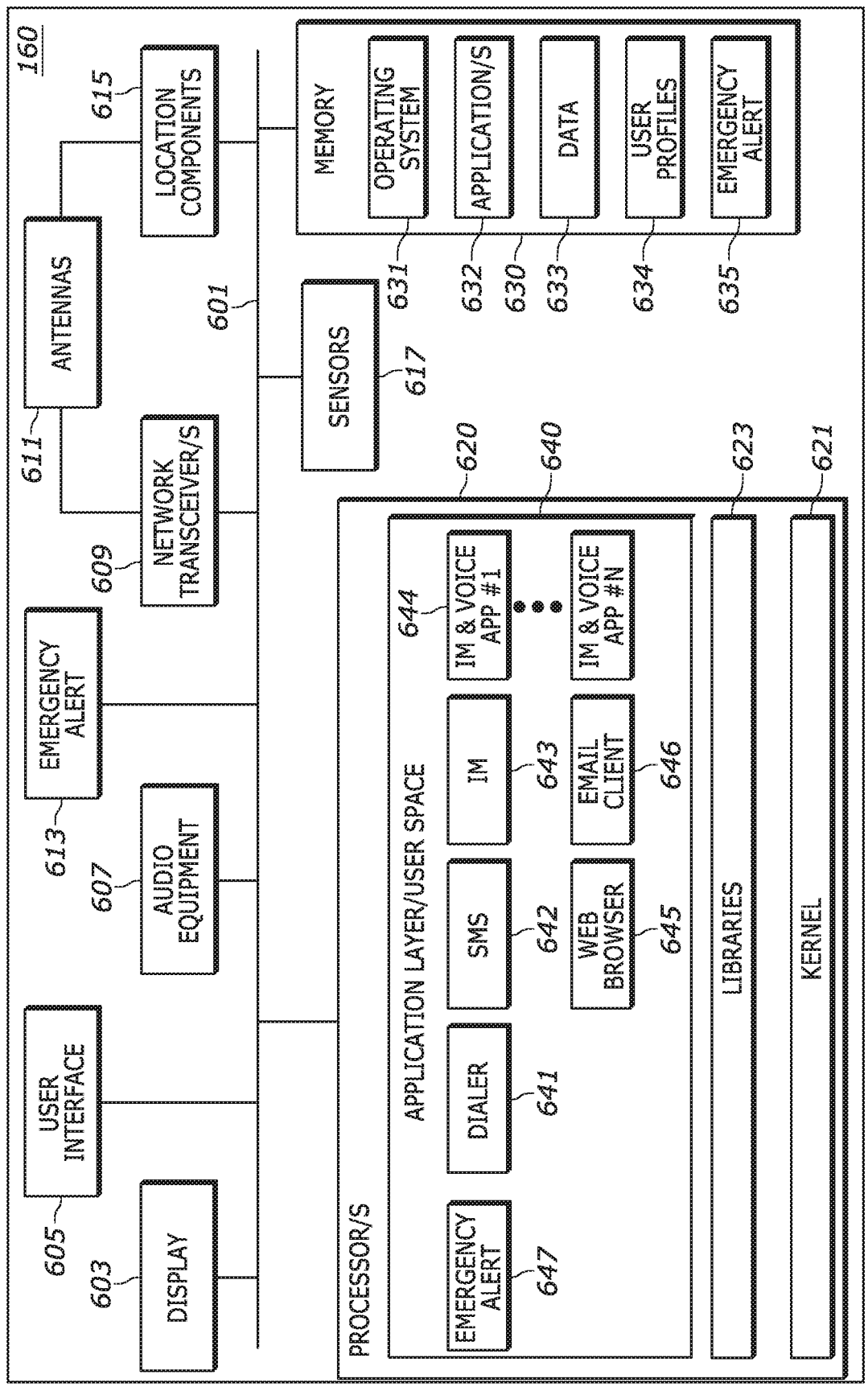
FIG. 6 is a block diagram providing an example of internal components of a device which may be used as an emergency caller device or to send an emergency alert.

FIG. 6 is a block diagram providing an example of internal components of a device 160. It is to be understood that FIG. 6 is an example only, and that a given device 160 may have more components, less components, or different components than shown, depending on the specific function and type of device. Further, depending on the type of device, there may be hardware only, hardware and firmware, hardware and software, etc. and may therefore be implemented in various ways not limited by the components shown in the FIG. 6 example. The example device 160 may be, but is not limited to: a mobile or cellular phone such as a smartphone; a wearable device such as a medical information bracelet, a fitness tracker or a smartwatch; a computer, laptop, or tablet; a vehicle console; an Internet of Things (IoT) device, such as a home assistant (e.g., a connected speaker) or a connected sensor such as a connected smoke and carbon monoxide alarm, a burglar alarm, etc.; or a walkie-talkie or two-way radio; etc. The example device 160 may include a display 603, a user interface 605, audio equipment 607, network transceiver/s 609, antennas 611, location components 615, sensors 617, at least one processor 620, and at least one non-volatile, non-transitory memory 630 in addition to RAM. Network components may include one or more wireless network transceivers for wireless communication such as for cellular communication, Wi-Fi™, Bluetooth™, etc. The memory 630 stores executable instructions and data such as executable instructions for an operating system 631, various applications 632 and an emergency alert application 635 in some implementations. The memory 630 also stores data 633 which may provide a location data cache and a user data cache. The device 160 may, in the case of mobile telephones, include a SIM card or other removable, replaceable memory components in addition to memory 630. The location data cache be used to store locations generated by the one or more location components 615 which may include a GPS chipset, triangulation processing, or other location determination technology, etc. User profiles 634 stored in memory 630 may contain information related to specific devices user configuration preferences, data sharing permissions, etc.

The processor 620 may be implemented as one or more microprocessors, ASICs, FPGAs, microcomputers, microcontrollers, digital signal processors, central processing units, state machines, logic circuitries, and/or devices that manipulate signals based on operational instructions. Among other capabilities, the processor 620 is configured and operative to fetch and execute computer-readable instructions (i.e. executable instructions) stored in the memory 630. For example, the applications 632 executable instructions, when executed by the at least one processor 620, may provide, a dialer application 641, a short-message-service (SMS) application 642, an instant message (IM) application 643, a web browser 645, an email client 646 and one or more IM and voice applications 644 which may each provide IM and voice call capability separately or in combination. The IM and voice applications 644 are referred to as "over-the-top" applications because the operate within the application layer of a mobile operating system. The operating system 631 executable instructions, when executed by the at least one processor 620, may provide a kernel 621, libraries 623 (also referred to as "application programming interfaces" or APIs) and an application layer 640 or user space within which the various applications are executed.

All of the components of the device 160 are operatively coupled by an internal communication bus 601. The display 603 is operatively coupled to the user interface 605 or may be considered a part of the user interface 605 such as in the case of a touchscreen which is both a display and a user interface in that it provides an interface to receive user input or user interactions. In some devices, the display 603 may not include a touchscreen, but may include one or more lights, indicators, lighted buttons, or combinations of these. The user interface 605 may also include physical buttons such as an on/off button or volume buttons, and the audio equipment 607 may include a microphone and a speaker.

The example device 160 may also include various accessories that allow for additional functionality. Such accessories (not shown) may include one or more of the following: a microphone, a camera, speaker, a fingerprint scanner/reader, health or environmental sensors, a USB or micro-USB port, a headphone jack, a card reader, a SIM card slot, or any combination thereof. The one or more sensors may include, but are not limited to: a gyroscope, and an accelerometer which may be incorporated into an Inertial Measurement Unit (IMU); a thermometer; a heart rate sensor; a barometer; or a hematology analyzer, or some other type of biometric sensor.

An emergency alert component 613 may be an ASIC or may be implement as, or in conjunction with, an emergency alert application 647 where the emergency alert application 635 executable instructions are stored in memory 630 and executed by the processor 620. The emergency alert component 613 may be configured and operative to record user data, such as a name, address, or medical data of a user associated with the device 160. The emergency alert component 613 may also detect an emergency using features of the device 160 for example, when a user places an emergency call on a device that has phone call capabilities. The emergency alert component 613 may also work in conjunction with "fall detection" such as in a medical bracelet which uses the sensors 617, such as an IMU (inertial-measurement-unit), to detect if the wearer of the bracelet has fallen and to initiate an emergency call or emergency alert accordingly. The emergency alert component 613 may also work in conjunction with sensors 617 such as biometric sensors to detect for example, a cardiac event or some other critical health or safety event and to initiate an emergency call or emergency alert accordingly.

A device 160 user may initiate an emergency alert 105 by interacting with the user interface 605, or the emergency may be detected by sensors 617. In response to detecting an emergency alert or a request for assistance, such as a via native dial 9-1-1 call via the dialer application 641 (which is the phone's native dialer), which may be generated or sent by the device 160, the emergency alert component 613 may send a notification to the emergency network. The notification may be sent as an HTTP post containing information regarding the emergency request for assistance. The notification may include a location (e.g., a device-based hybrid location) generated by or for the electronic device. In response to detecting an emergency request generated or sent by the device, the emergency alert component 613 may send user data to the emergency network.

Figure 7:
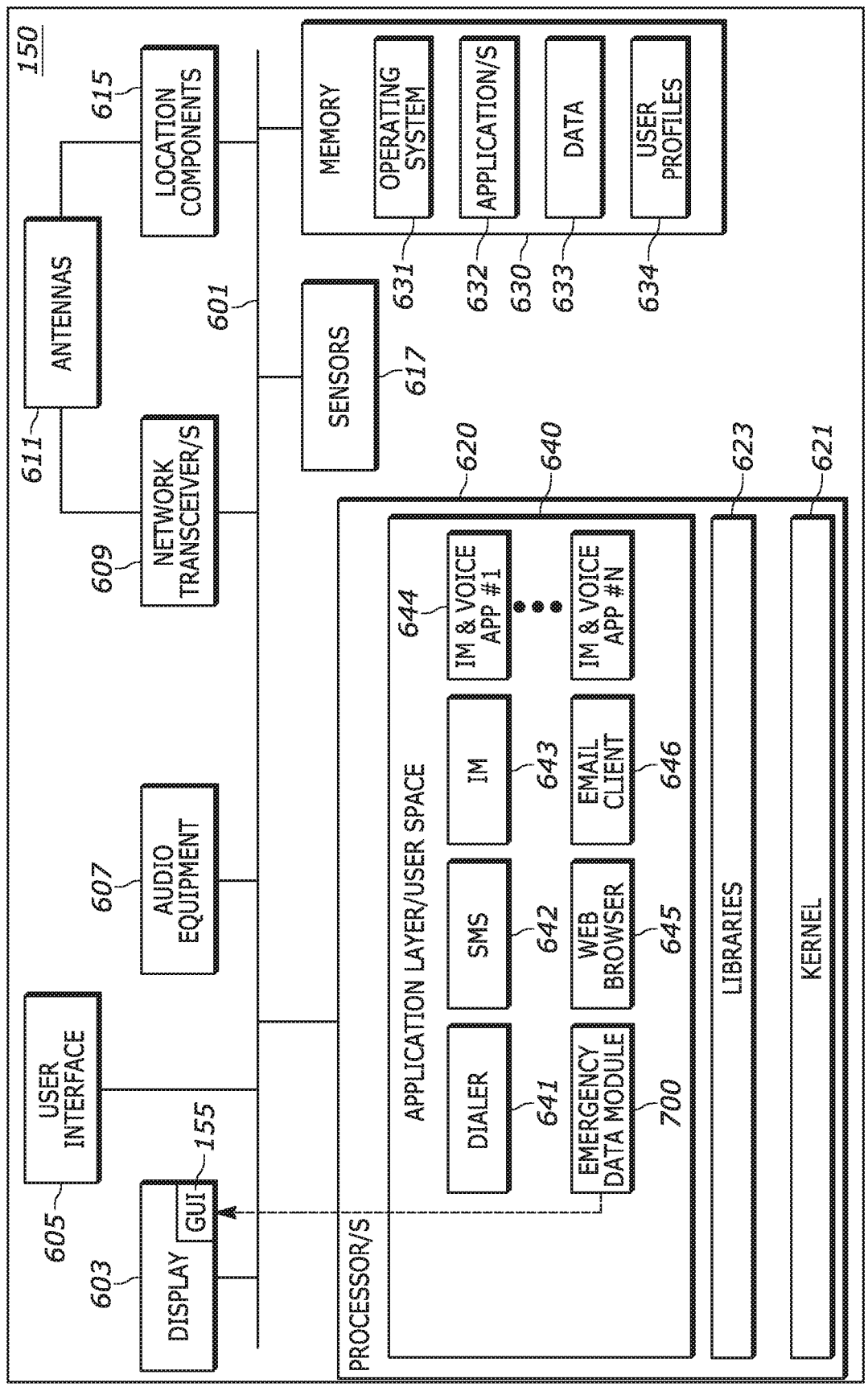
FIG. 7 is a block diagram providing an example of internal components of an emergency responder device which may be used to receive emergency data.

FIG. 7 is a block diagram providing an example of internal components of an emergency responder device 150 which may be used to receive emergency data. The internal components of the emergency responder device 150 are similar to the internal components of device 160 described with respect to FIG. 6. However, the emergency responder device 150, may include an emergency data application 700 that provides the GUI 155 for displaying emergency data including medical data, location data, etc. Emergency responder devices 150 are designed to display emergency data related to incidents within authoritative, administrative or assigned jurisdiction of the specific responder, and for which proper credentials are provided depending on the type of emergency data requested. The credentials of the responders may be matched to one or more geofences and incidents with current location within the geofences are displayed. Emergency responder devices 150 may display incidents based on a proximity radius on an interactive map. For example, a proximity radius may be within 10 meters to 5 kms, between 50 meters to 1000 meters, for example 500 meters. As the responder moves towards an area, new incidents within the proximity radius may be "unlocked" and viewed.

The emergency responder devices 150 are operative to send emergency data requests 151 to the emergency data manager 100 and also authentication data. The emergency data manager 100 may send an authentication request 154 to an emergency responder device 150 prior to receiving authentication data. The authentication request 154 may be, for example, a GUI 155 prompt to enter an authentication code. The authentication code may be a numerical code, a pattern, a biometric identifier, or a combination of these. The biometric identifier may be obtained from a patient at the scene of an emergency or may be a biometric that identifies the emergency responder. For example, either a device 160 owned by a bystander, or an emergency responder device 150, may receive an authentication request 154. In that case, where information is being obtained from a patient, the authentication request 154 may be a GUI prompt to scan an authentication code such as, but not limited to, a bar code, QR code, or RFID code on a medical bracelet or some other mechanism or a static code such as obtainable from a label, identification card, etc. In some implementations, an authentication code may be a dynamic code that may be generated by the emergency data manager 100, or by another server, using random or pseudorandom code generation techniques. For data security, the generated authentication code may be conveyed to a device, that allegedly sent an emergency data request 151 to the emergency data manager 100, by using SMS (short message service), email, a callback, etc. The emergency responder devices 150 may have biometric sensors or may be operative to connect to biometric sensor accessories such as, but not limited to, photoplethysmography sensors, fingerprint scanners, palm print scanner, facial recognition, retinal or iris scanners, hand geometry detection, ear geometry detection, odor/scent detection, DNA, behavior characteristics, or other biometric sensors, etc. A biometric identifier may be obtained from any of such biometric sensors or biometric sensor accessories and may be a combination of two or more biometric sensor measurements. If the emergency responder device 150 user is authorized, then the emergency data manager 100 will respond to an emergency data request 151 by providing emergency data 157 from various emergency data databases 120. The emergency responder devices 150 each have a web browser application or other application that provides the GUI 155 for displaying emergency data 157. The emergency data databases 120 may include, but are not limited to, location data 121, medical data 123 and other emergency data 125. Emergency data requests may also be sent from the GUI 143 during call handling procedures, emergency dispatch procedures or both, and emergency data requests 151 may be sent from the GUI 155 by an emergency responder device 150. Authentication data may also be sent by the GUI 155, or may be sent automatically by the emergency responder device 150 as part of, or in conjunction with, an emergency data request 151 initiated by an emergency responder device 150 user.

In response to an emergency data request 151 from an emergency responder device 150, the emergency data manager 100 may request authentication data prior to sending any protected data. Alternatively, an emergency responder device 150 may send authentication data to the emergency data manager 100 at the time of sending the emergency data request 151. If the authentication data authenticates the emergency responder device 150, then the emergency data manager 100 sends an appropriate response including relevant emergency data 157 to via an encrypted pathway. The emergency data request 151 may be, for example, an HTTP-Enabled Location Delivery (HELD) message and the response from the emergency data manager 100 or the emergency data manager 100 may be a Presence Information Data Format Location Object (PIDF-LO) in accordance with NENA requirements.

For some emergency networks, emergency data requests 151 may be sent over public networks using API access keys or credentials. Transport Layer Security (TLS) may be used in the emergency data requests to the emergency data manager 100 and for sending emergency data 157 to emergency responder devices 150 for encryption security. The emergency responder device 150 may display the emergency data 157 using a web portal GUI or an application GUI.

FIG. 8 is a flowchart showing a method of operation of an emergency data manager 100 in accordance with various embodiments. The method of operation begins, and in operation block 801 the emergency data manager 100 obtains a device identifier which may be, for example, a phone number, from an emergency call. Particularly for smartphones 107, when a smartphone 107 initiates an emergency session 108, sends an emergency alert 105 or places an emergency call 103, location data is sent from the device to the location data database 121 and is pushed to the emergency data manager 100. The location information includes a device identifier which may be used by the emergency data manager 100 to search other of the databases 120 for related information and to correlate available information with the device identifier.

In operation block 803, the emergency data manager 100 communicates with the medical data database 123 to obtain a list of candidate medical profiles corresponding to the device identifier which may be a phone number. The candidate profiles are anonymized candidate profiles that do not expose protected data including the personally identifiable information related to the patient. The candidate medical profiles may be obtained by the emergency data manager 100 in response to an emergency data request 151 from an emergency responder device 150. The emergency data request 151 may be initiated by the emergency response device 150 using GUI 155, or by an emergency network entity using the emergency response logic 144 and GUI 143. In operation block 805, the requesting device 150 via GUI 155, or the workstation 140 via GUI 143, receives a candidate selection input. In response to the candidate selection input in operation block 805, the emergency data manager 100 will obtain the non-anonymized medical profile for the selected candidate medical profile as shown in operation block 807. The non-anonymized medical profile is then displayed on the GUI 143, GUI 155 or both, as shown in operation block 809. The method of operation then terminates.

FIG. 9 is another method of operation of the emergency data manager 100 in which an emergency alert 105 is received by the emergency data manager 100. The method of operation begins, and in operation block 901, an emergency alert 105 is received by the emergency data manager 100. In operation block 903, the emergency data manager 100 receives a medical ID along with the emergency alert 105. For example, the medical ID may be sent by a medical bracelet 109 that is wirelessly coupled to an in-home system that is operative to send the emergency alert 105. Alternatively, the medical ID may be sent by a mobile device such as a smart phone 107. In operation block 905, selection input is received to select the anonymized candidate profile at either GUI 144 or GUI 155, in order to receive non-anonymized medical data. In operation block 907, in response to the anonymized candidate profile selection input in operation block 905, the emergency data manager 100 communicates with the medical data database 123 to obtain a non-anonymized medical profile for the selected candidate. In operation block 909, the non-anonymized medical profile is displayed on either the GUI 143, the GUI 155 or both. The method of operation then terminates.

Figure 10:
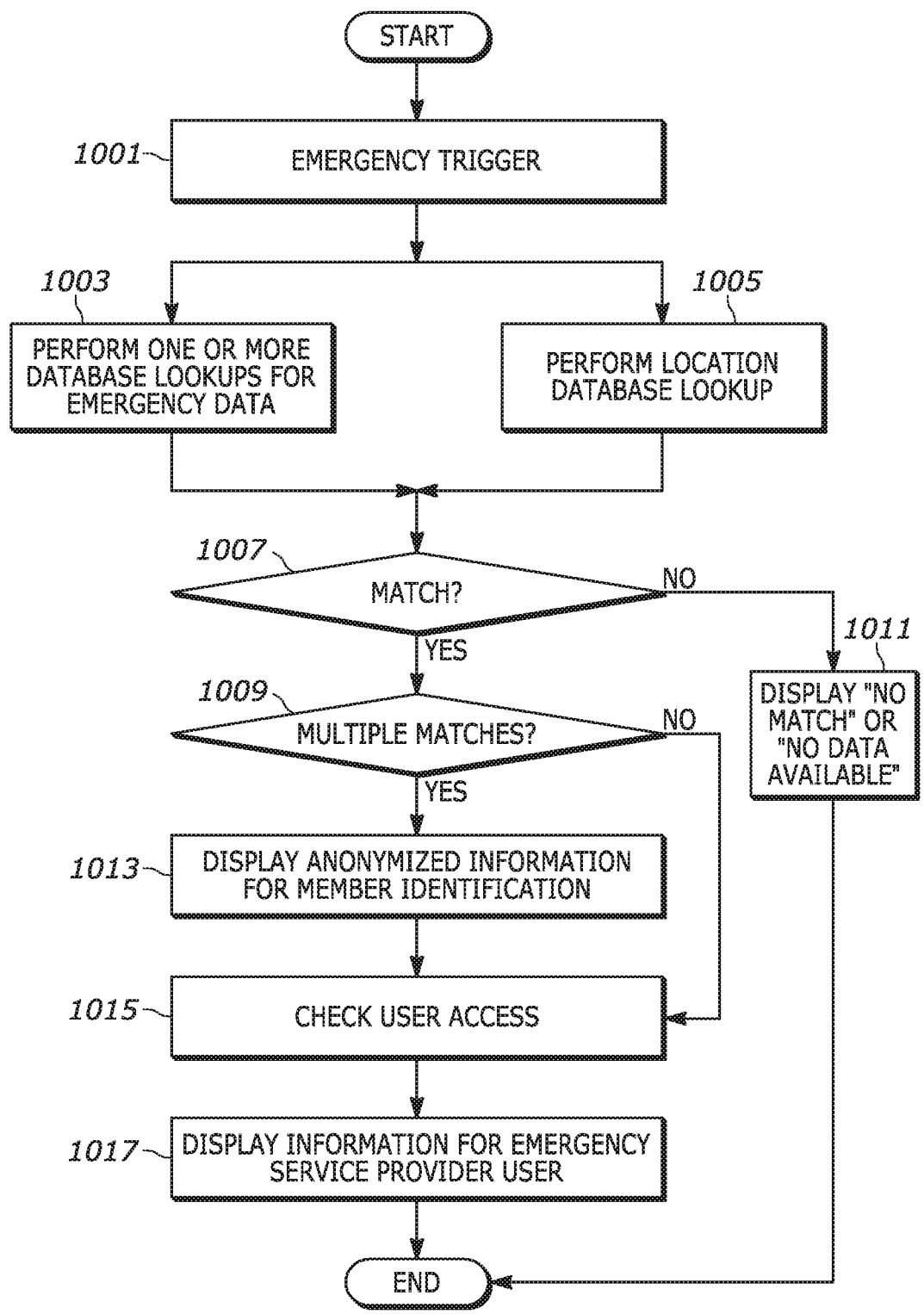
FIG. 10 is a flowchart showing a method of operation of an emergency data manager in accordance with various embodiments.

FIG. 10 provides another example method of operation of an emergency data manager 100 in accordance with various embodiments. The method of operation begins and in operation block 1001 an emergency trigger is received by the emergency data manager 100. The emergency trigger may be an emergency alert 105, or may be an emergency call 103, or some other trigger. In operation block 1003, the emergency data manager 100 will perform one or more database lookups for emergency data using the various databases 120, and the protected data database 190. In operation block 1005, the emergency data manager 100 will also perform a location database 121 lookup, or will have location data pushed to it by the location database 121 in response to an emergency alert 105 or emergency call 103.

In decision block 1007, if a match is found that matches any of the data to information contained in the emergency trigger, then the method of operation proceeds to decision block 1009. The emergency trigger may contain information such as, but not limited to, a medical ID, caller ID, location data, or some other data that may be related to the emergency trigger. If no match is found in decision block 1007, then the method of operation proceeds to operation block 1011 and displays a message such as "no match" or "no data available" or some equivalent. The method of operation then terminates.

Returning to decision block 1009, if multiple matches are found during the database lookups, then the method of operation proceeds to operation block 1013 and displays anonymized information from number identification. In operation block 1015, user access is checked to determine whether authorization exists for accessing protected data or other confidential data. If multiple matches are not found at decision block 1009, the method of operation proceeds directly to operation block 1015 and determines whether authorization exists. If authorization exists in operation block 1015, then in operation block 1017 the non-anonymized information is displayed for the emergency service provider user. The emergency data may be displayed for example and GUI 143, GUI 155 or both. The method of operation then terminates as shown.

Figure 11:
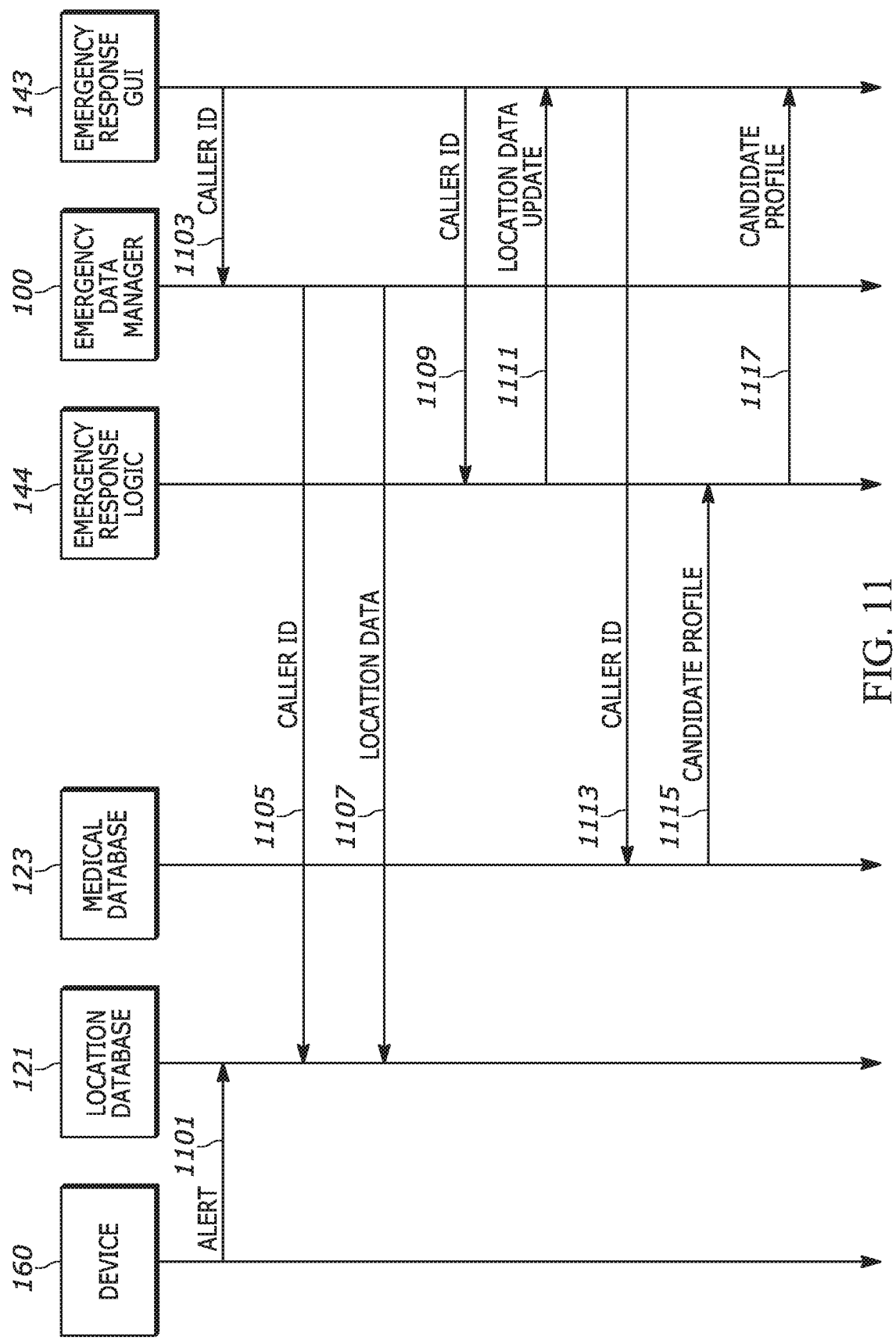
FIG. 11 is a message flow diagram showing a method of operation of an emergency data manager in accordance with various embodiments.

FIG. 11 is a message flow diagram showing messaging between a device 160, an emergency data manager 100, emergency response logic 144 in an emergency network entity, and various databases in accordance with various embodiments. An emergency alert message 1101 is sent from a device 160 to the various databases 120 and, in particular, to the location database 121. In some cases, the location data from location database 121 is pushed to the emergency data manager 100 without requiring any request for the location data. The emergency alert initiates a call to an emergency network, where personnel may enter the device identifier into the GUI 143 on a workstation.

A user identifier, which may be a phone number, name, medical identifier, etc., is associated with an emergency alert and may be received from the emergency network entity GUI 143 (e.g. at a PSAP). For example, a query from an emergency network, such as a PSAP, may be received including a user identifier at the emergency data manager 100. The emergency data manager 100 performs a database query using the user identifier received in message 1103, and message 1105 is sent to the location database 121 to perform a database search. The requesting party may be subscribed to the user identifier, such as a phone number, and location updates are received without the need for additional queries. The emergency data manager 100 may receive location data 1107 and updates from the location database 121. The emergency response GUI 143 provides the user identifier to the emergency response logic 144 as shown by message 1109. The emergency response logic 144 provides a location data update 1111 and the location information is displayed by the emergency response GUI 143. Emergency response GUI 143 also provides the caller ID to the medical database 123 is shown by message 1113. In response, the medical database 123 provides candidate profile 1115 (which may be anonymized if no credentials are provided) to the emergency response logic 144 and the candidate profile 1117 is displayed on the emergency response GUI 143. The caller ID associated with the medical ID may be the caller ID of the patient corresponding to the medical ID, or may be an emergency contact or a caretaker for the patient having the medical ID. In either case, the medical database 123 includes an association of the caller ID to the medical ID so that the medical data can be obtained in the event of an emergency alert or emergency call related to the patient. In that case, non-anonymized medical data will be displayed on the emergency response GUI 143.

Figure 12:
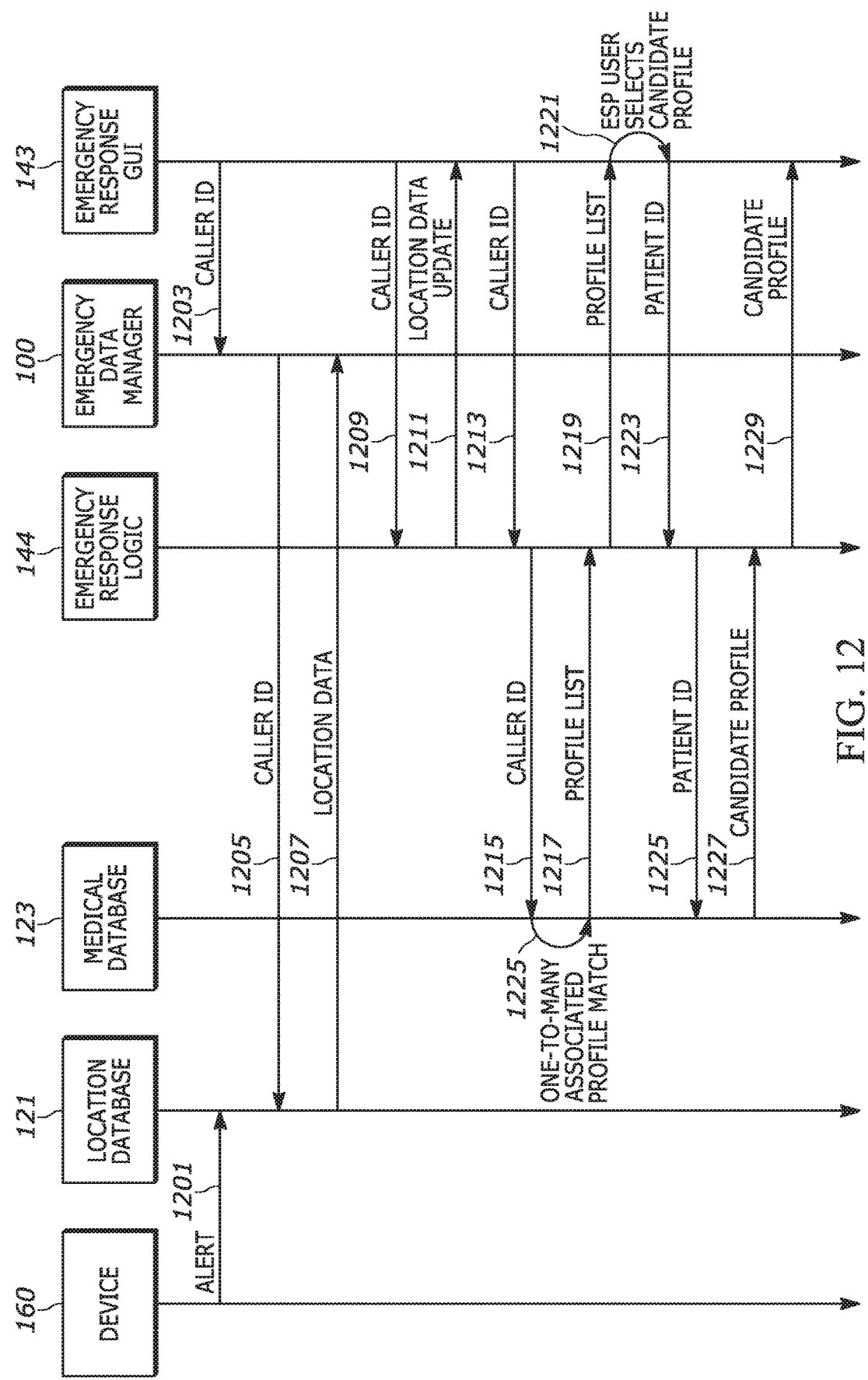
FIG. 12 is a message flow diagram showing a method of operation of an emergency data manager in accordance with various embodiments.

FIG. 12 is a message flow diagram showing messaging between a device 160, an emergency data manager 100, emergency response logic 144 in an emergency network entity, and various databases in accordance with various embodiments. in accordance with various embodiments in which multiple medical profiles may be associated with the same caller ID. An emergency alert message 1201 is sent from a device 160 to the location database 121 and caller ID received at the emergency response GUI 143 sent to the emergency data manager 100 as shown by message 1203. The emergency data manager 100 uses the caller ID in query message 1205 to the location database 121 and receives location data 1207. The emergency response GUI 143 provides the caller ID 1209 to the emergency response logic 144 and receives the location data update 1211 for display. The caller ID 1213 provided by the emergency response GUI 143 to the emergency response logic 144 and is forwarded in a query message 1215 to the medical database 123. Medical database 123 makes a one to many associated profile match 1225 and returns the profile list 1217 to the emergency response logic 144. The profile list 1219 is a list of anonymized candidate profiles that provide anonymized patient information without exposing protected data including the personally identifiable information related to the patient. The anonymized candidate profiles provide enough information for emergency network staff to recognize and select which specific non-anonymized profile is required to respond to the emergency. The profile list 1219 is then provided by the emergency response logic 144 to the emergency response GUI 143, and a user selection input 1221 selects a candidate profile such that non-anonymized data may be sent. The patient ID 1223 associated with the selected candidate profile is forwarded by the emergency response logic 144 as query message 1225 to the medical database 123, and medical database 123 returns the appropriate non-anonymized candidate profile 1227 to the emergency response logic 144. The non-anonymized candidate profile 1229 is then displayed by the emergency response GUI 143.

Figure 13:
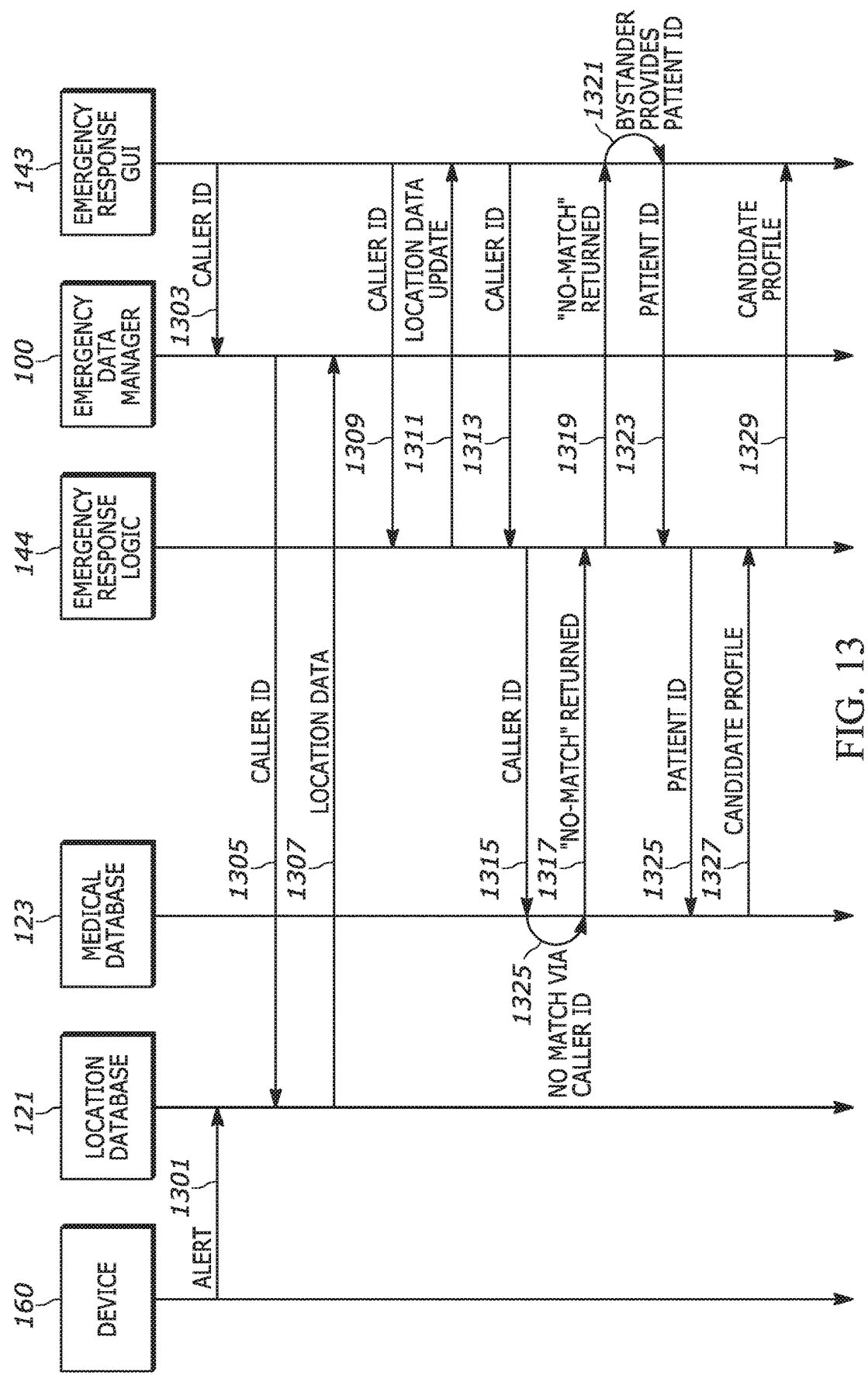
FIG. 13 is a message flow diagram showing a method of operation of an emergency data manager in accordance with various embodiments.

FIG. 13 is a message flow diagram showing messaging between a device 160, an emergency data manager 100, emergency response logic 144 in an emergency network entity, and various databases in accordance with various embodiments in which the caller ID does not have a corresponding medical profile associated. In this situation, a bystander or an emergency responder provides the patient ID, or medical ID to the emergency network personnel. An emergency alert 1301 is sent from a device 160 with the location database 121. The emergency response GUI provides the caller ID 1303 to the emergency data manager 100 which uses the caller ID inquiry message 1305 to the location database 121 and receives location data 1307. The emergency response GUI 143 provides the caller ID 1309 to the emergency response logic 144 and receives the location data update 1311. The caller ID 1313 is also forwarded by the emergency response logic 144 as a query message 1315 to the medical database 123. The medical database 123 determines that there is no match via caller ID as shown by operation 1325, and returns a "non-match" message 1317 to the emergency response logic 144. The emergency response logic 144 displays the non-match return message 1319 and emergency response GUI 143. At that point, an emergency responder or a bystander performs the operation 1321 of providing the patient ID to the emergency network personnel who may then enter it into the emergency response GUI 143 or may receive it via text message, or via some other mechanism. The patient ID 1323 is then provided to the emergency response logic 144, which then uses the patient ID that provides message 1325 to the medical database 123 to receive the medical candidate profile 1327. The candidate profile 1329 is then displayed by the emergency response logic 144 on the emergency response GUI 143.

FIG. 14 is a table with example levels of importance that emergency network personnel such as telecommunicators and emergency medical technicians (EMTs) may attribute to various pieces of medical data. The first column 1405 indicates the medical data. The column 1407 indicates the treatment of the data by telecommunicators and column 1409 indicates the treatment of the medical data by EMTs. The medical data that may be displayed on the emergency response GUI 143 or emergency response GUI 155 includes, but is not limited to: name, age, gender, and any emergency contacts, and data sorted into categories such as a medical information overview that may show for example any implants, pacemakers, history of memory impairment, history of seizure disorders, whether the patient is diabetic and medical history information such as allergies, medications.

Figure 15:
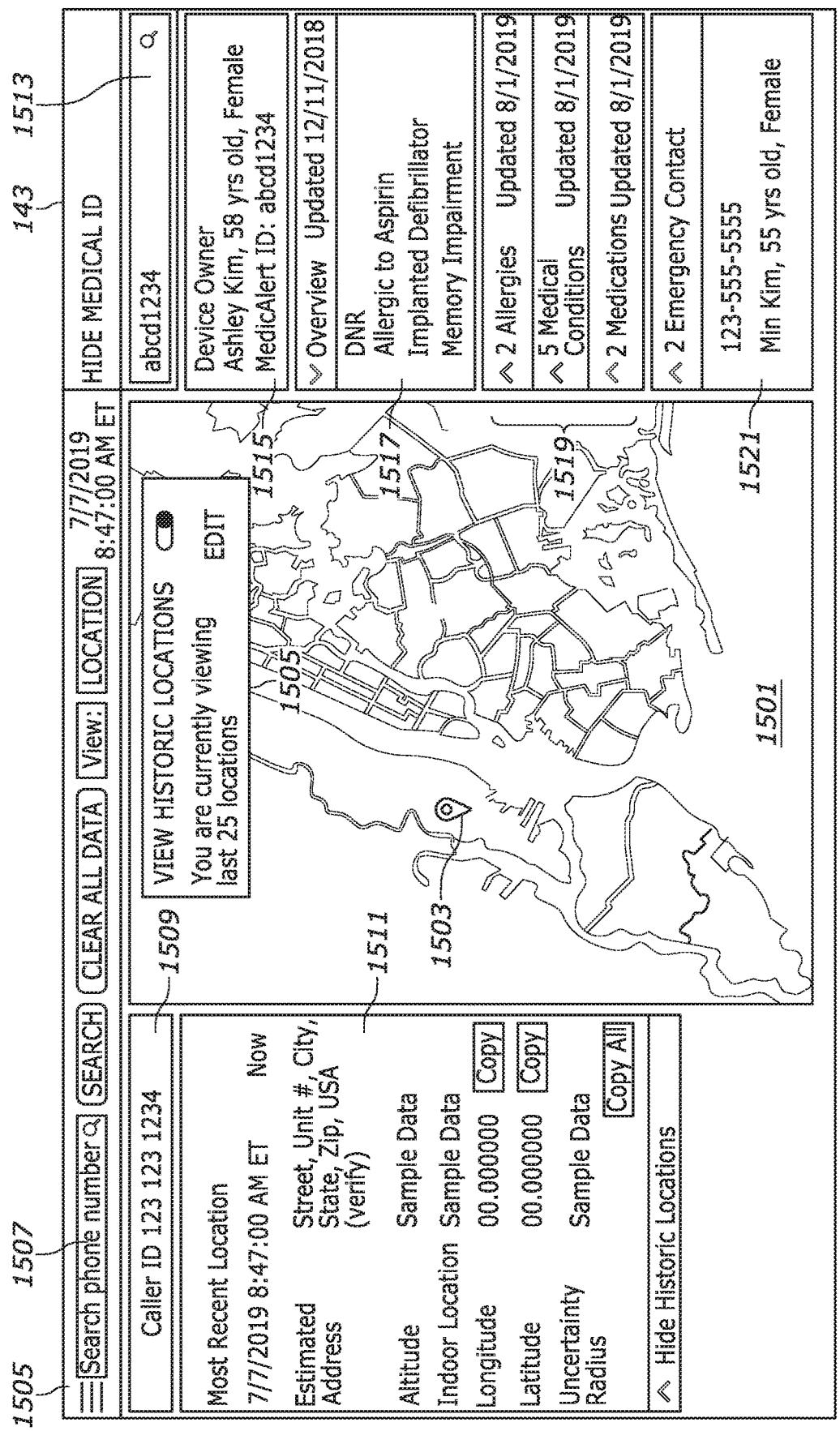
FIG. 15 is an example diagram of an emergency response graphical user interface (GUI) in accordance with an embodiment.

FIG. 15 an example diagram of an emergency response graphical user interface (GUI) in accordance with an embodiment. FIG. 15 depicts an example GUI window 1500 depicted to a telecommunicator when searching for the referenced medical ID. The GUI window 1500 is one example window that may be displayed by the GUI 143. The GUI window 1500 includes a menu bar 1505 with a search field 1507 operative to search for a phone number. A caller ID field 1509 provides a phone number of an incoming emergency caller or a phone number associated with a received emergency alert 105. A location field 1511 provides location data such as, but not limited to, address, and coordinates related to the emergency caller. A map area 1501 provides a map view with a pinpoint locator 1503 designating the specific address or coordinate location based on the location data shown in the location field 1511.

A medical identifier search field 1513 enables a search for patient medical data associated with a medical identifier such as a medical bracelet ID number, etc. In situations where the patient is also the owner of the device that generated the emergency call or emergency alert, the device owner information will be shown in a device owner information field 1515. Medical data associated with the patient's medical identifier will be displayed in a medical data overview field 1517 and specific information will be displayed in medical fields 1519 which can be expanded to show all details associated with specific entries such as, but not limited to, allergies, medical conditions, medications, etc. An emergency contacts field 1521 shows information for any know emergency contacts for the patient.

Figure 16:
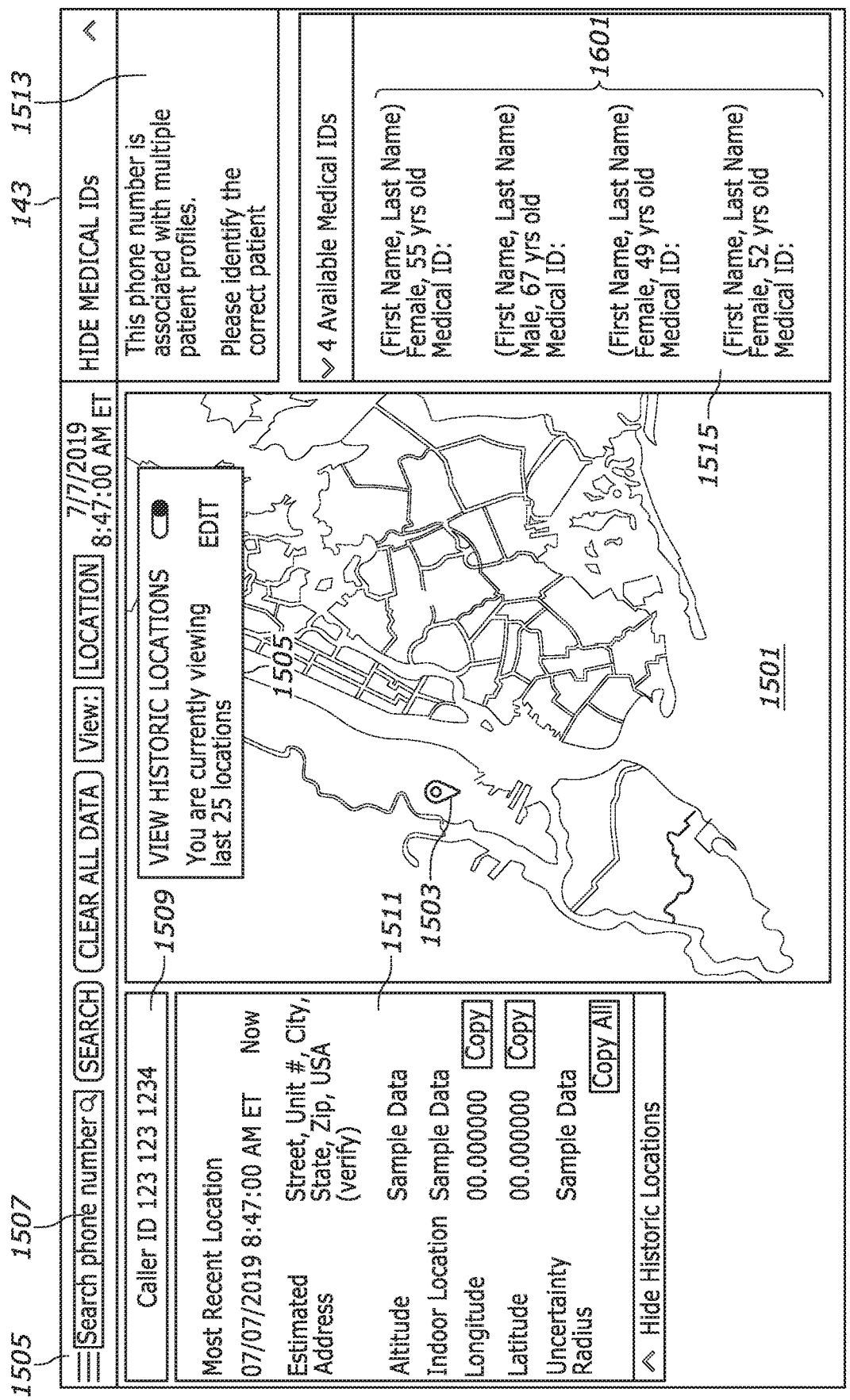
FIG. 16 is an example diagram of an emergency response graphical user interface (GUI) in accordance with an embodiment.

FIG. 16 depicts an example of the GUI window 1500 when multiple medical identifiers match a single device phone number. The GUI window 1500 is one example window that may be displayed by the GUI 143. In that case, the telecommunicator is shown the available medical profiles in an anonymized candidate profile list 1601 in the device owner information field 1515 or in a different field in some embodiments. The medical identifier search field 1513 provides a notification that the phone number is associated with multiple patient profiles. The anonymized candidate profile list 1601 provides age and gender information such that the telecommunicator may select the correct profile for the person in need of emergency assistance. After the telecommunicator selects an anonymized candidate profile from the profile list 1601, non-anonymized medical information for the selected patient is displayed similar to the display shown in FIG. 15.

Thus, the described emergency response logic and associated GUIs provide differential access, based on credentials, to medical data during an emergency, e.g., by an emergency network in order to avoid and limit exposure of protected data related to a patient or user and corresponding to a non-anonymized protected data profile such as, but not limited to, a medical profile for the patient or user. In certain implementations, an emergency session/call can be detected, an emergency alert can be received, etc., as described herein. Using a user identifier (e.g., a phone number, or medical ID) various databases (e.g., a medical database 123 as depicted in FIG. 1 and FIG. 2) can be searched for medical data identified as being associated with the person in the emergency, as opposed to data associated with the bystander, emergency contact, etc. Such identified emergency data can then be displayed to an emergency service provider (emergency network) user. In certain implementations, the emergency network user can be determined to have access to the medical data based on credentials, admin preferences, etc.

In certain implementations, the various databases can maintain information associated with a phone number. Such information can include fields such as: name, gender, age, ID number, "Public" inscription such as the ID number on a bracelet, and short freeform text of medical info relevant to emergency network such as allergy information included on the bracelet.

In certain scenarios there may be requirements for accessing private medical data or other protected data and differential access may be granted based on credentials and roles. For example, in certain scenarios the emergency data manager 100 may provide access to medical data during an emergency to authorized users. In other words, the referenced medical data can be accessed, stored, transmitted, and displayed in a manner to protect personally identifiable information (PII) or protected health information (PHI).

In certain situations, the user identifier or medical identifier may be provided by a bystander caller, or by an emergency responder. Emergency network personnel or an emergency responder may query for emergency data using the user identifier and receive medical data or other protected data based on the credential or role of the emergency network user. Accessible data may include private, protected data, which may include, but is not limited to, user location, profile data, user files such as images, voice recordings, video, and etc., and also metadata such as, but not limited to, time stamp, volume of calls, etc.

Protected data can be displayed in an anonymized way, so as to confirm the identity of the person in the emergency. A trigger can be used to obtain data such as expiration of a timer, an emergency call, an emergency notification, a check-in request, etc. A timer may be used to periodically query a protected data database 190 for additional data which may be private or sensitive. The query to protected data database 190 may be made upon receipt of an emergency call from a particular phone number or a particular user identifier in the case of a text message, chat session or other emergency communication received other than a phone call. An emergency alert 105, such as but not limited to, a medical bracelet fall-detection indication, a panic button, an alarm signal or other initiation of an emergency session, etc., may also initiate sending a query to protected data database 190. Additionally, a check-in request can be provided by an emergency contact of an individual on an emergency registry.

As used herein, an "identifier" refers to a way to identify a device associated with a specific user. The device identifier may include phone number, email address, physical address, coordinates, IMEI number, IP address BSSID, SSID or MAC address. A "medical identifier" refers to a way to identify a patient and may be incorporated into a device such as a medical bracelet, RFID chip, smartcard, barcode, QR code, or some other form of encoding, etc.

As used herein, an "emergency alert" refers to a communication relating to an emergency or non-emergency situation. An emergency alert may be an emergency request for assistance (e.g., the request is associated with an emergency situation), and may include an emergency indication, which may be an indicator of a traffic accident, a police emergency, a medical emergency, a fire emergency, or some other emergency, etc. An emergency alert associated with a non-emergency situation may be, for example, a request for a tow truck after car breaks down. An emergency alert may be associated with a device sending the alert, or may be associated with a device not sending the alert, such as when a proxy request is made on behalf of a second device and/or a member device in a group of devices. As used herein, an emergency alert is "associated" with a device or user when the emergency alert relates to an emergency or non-emergency situation involving the device or user. An emergency alert may include data associated with a device or user thereof, and may include data associated with an device sending the alert or another device. For example, an emergency alert may include data associated with a device, wherein the data set may include current and/or past location data. In another example, the data set may include current and/or past health data associated with the user of a device. An emergency alert may be sent and/or received separately from data associated with a device. For example, an alert may be sent first, and the recipient may subsequently query the device that sent the alert for data associated with the emergency and/or device or user involved in the emergency as part of an emergency flow script.

As used herein, an "emergency responder" refers to any person or persons responsible for addressing an emergency situation. An emergency responder may be responsible for a particular jurisdiction such as a municipality, a township, a county, etc., also referred to as its authoritative jurisdiction. An emergency responder may be assigned to an emergency by an emergency network such as, but not limited to, an emergency dispatch center (hereinafter, "EDC") or a PSAP. An emergency responder responds to a request for emergency assistance placed by a user via a communication device. Emergency responder may include firefighters, police officers, emergency medical personnel, community volunteers, private security, security personnel at a university, or other persons employed to protect and serve the public and/or certain subsets of the population.

In many cases, the emergency responder communicates with the dispatching organization such as a PSAP, through a responder device. In many cases, the responder device is a mobile device that the responder carries such as a smartphone, tablet, radio, walkie talkie, or a vehicular console, etc. The responder devices are configured to receive and update emergency data through secure and encrypted pathways. In addition, the responder devices may include security and privacy measures to protect emergency information.

As used herein, a public safety answering point (PSAP) refers to a call center responsible for answering calls to an emergency telephone number for police, firefighting, and ambulance services. Trained telephone operators (also referred to as call-takers) are also usually responsible for dispatching these emergency services. The Federal Communications Commission (FCC) of the United States government maintains a PSAP registry. The registry lists PSAPs by an FCC assigned identification number, PSAP Name, State, County, City, and provides information on any type of record change and the reason for updating the record. The FCC updates the registry periodically as it receives additional information.

As used herein, "medical data" refers to medical information associated with a user of a device. Medical data may include medical history such as, for example, past illnesses, surgery, food and/or drug allergies, diseases, disorders, medical diagnostic information (e.g., genetic profile screen), or any combination thereof. Medical data may include family medical history (e.g., family history of breast cancer), current health information such as, for example, current symptoms, current medications, and/or current illnesses or diseases, and may include user age, height, weight, blood type, and/or other biometrics.

As used herein, "user data" refers to general information associated with a user of a device. User data may include user identity, user name, height, weight, eye color, hair color, ethnicity, national origin, religion, language(s) spoken, vision (e.g., whether user needs corrective lenses), home address, work address, occupation, family information, user contact information, emergency contact information, social security number, alien registration number, driver's license number, vehicle VIN, organ donor (e.g., whether user is an organ donor), or any combination thereof. User data may be obtained via user input.

As used herein, "sensor data" refers to information obtained or provided by one or more sensors. In some instances, a sensor is associated with a device (e.g., user has a communication device with a data link via Bluetooth with a wearable sensor, such as, for example, a heart rate monitor or a pedometer). Accordingly, the device obtains sensor data from the sensor (e.g., heart rate from the heart rate monitor or distance traveled from the pedometer). In some instances, the sensor data is relevant to an emergency situation (e.g., heart rate during a cardiac emergency event). A sensor and/or sensor device may include an acoustic sensor, a breathalyzer, a carbon dioxide sensor, a carbon monoxide sensor, an infrared sensor, an oxygen sensor, an ozone monitor, a pH sensor, a smoke detector, a current sensor (e.g., detects electric current in a wire), a magnetometer, a metal detector, a radio direction finder, a voltage detector, an air flow meter, an anemometer, a flow sensor, a gas meter, a water meter, a Geiger counter, an altimeter, an air speed indicator, a depth gauge, a gyroscope, a compass, an odometer, a shock detector (e.g., on a football helmet to measure impact), a barometer, a pressure gauge, a thermometer, a proximity sensor, a motion detector (e.g., in a home security system), an occupancy sensor, or any combination thereof, and, sensor data may include information obtained from any of the preceding sensors. One or more sensors may be physically separate from a user device. The one or more sensors may authorize the user device to obtain sensor data. The one or more sensors may provide or send sensor data to the user device autonomously. The user device and the one or more sensors may belong to the same group of devices, wherein member devices are authorized to share data. A user device may include one or more sensors (e.g., user device is a wearable device having a sensor or sensing component).

As used herein, "emergency data" refers to data pertaining to an on-going or historical emergency. The emergency data may be generated at the time of the emergency. The emergency data may be generated before the emergency occurs and may be made accessible when the emergency occurs. Emergency data may include location data, particularly the current location of the emergency (often times based on the location of the user device). Because of privacy and security concerns, emergency data has to be stored, accessed, transmitted using security and privacy measures.

While various embodiments have been illustrated and described, it is to be understood that the invention is not so limited. Numerous modifications, changes, variations, substitutions and equivalents will occur to those skilled in the art without departing from the scope of the present invention as defined by the appended claims.

What is claimed is:

1. A method comprising:
   detecting an emergency at a cloud-based server by receiving an emergency alert from a mobile device, sent by the mobile device over an internet connection, where the emergency alert comprises mobile device hybrid location data generated by the mobile device and a mobile device identifier;
   providing by the cloud-based server to a public safety answering point (PSAP), an instance of a software-as-a-service emergency response application having a graphical user interface (GUI) associated therewith;
   pushing the emergency alert comprising the mobile device hybrid location data and the mobile device identifier to the instance based on the mobile device hybrid location data and displaying the emergency alert on the GUI at the PSAP;
   receiving protected medical profile data at the cloud-based server, corresponding to at least one patient medical identifier associated with the mobile device identifier contained in the emergency alert; and
   displaying an anonymized candidate profile list in the GUI at the PSAP having at least one list entry for the medical profile corresponding to the at least one patient medical identifier, the anonymized candidate profile not exposing protected medical information related to the patient medical identifier.

2. The method in claim 1, wherein retrieving protected medical profile data corresponding to at least one patient medical identifier, comprises:
   retrieving a plurality of anonymized candidate profiles corresponding to the at least one patient identifier, the anonymized candidate profiles providing anonymized protected medical information for a plurality of patients, without exposing protected medical information related to the plurality of patients.

3. The method in claim 1, further comprising:
   receiving a medical data request at the cloud-based server from an emergency responder mobile device associated with the PSAP and dispatched to a location based on the mobile device hybrid location data, the medical data request comprising the patient identifier and authentication data for the responder mobile device; and
   providing the protected medical information related to the patient medical identifier to the emergency responder mobile device in response to the medical data request and based on an authorization level specified in the authentication data to comply with access requirements for the protected medical information.

4. The method in claim 2, further comprising:
   displaying the anonymized candidate profiles on a display of the emergency responder mobile device in response to the medical data request;
   receiving a selection input corresponding to a selected one of the anonymized candidate profiles; and
   displaying non-anonymized protected medical information corresponding to the selected one of the anonymized candidate profiles on the display of the emergency responder mobile device in response to the selection input.

5. The method of claim 4, further comprising:
   retrieving and transmitting the non-anonymized protected medical information in compliance with requirements for protection of personally identifiable information (PII) and protected health information (PHI).

6. The method of claim 1, further comprising:
   receiving the patient medical identifier from a device of a bystander caller.

7. The method of claim 1, further comprising:
   receiving the medical data request from the emergency responder mobile device, the medical data request comprising emergency responder credentials; and
   providing limited access to the protected medical information by the emergency responder mobile device based on data access limitations specified in the emergency responder credentials.

8. The method of claim 1, further comprising:
   receiving the medical data request from the GUI at the PSAP on behalf of the emergency responder mobile device, the medical data request comprising emergency responder credentials; and
   providing limited access to the protected medical information by the emergency responder mobile device based on data access limitations specified in the emergency responder credentials.

9. An emergency data manager comprising:
   a cloud-based server having an application server component, operative to provide a plurality of cloud-based, software-as-a-service emergency response application instances to a plurality of public safety answering points (PSAPs) via a graphical user interface (GUI) associated with each emergency response application instance;
   a network component, operative to provide Internet Protocol (IP) connections to the plurality of PSAPs and to a plurality of emergency data servers and databases; and
   at least one processor, operatively coupled to the network component, the at least one processor operative to:
      detect an emergency at the cloud-based server by receiving an emergency alert from a mobile device, sent by the mobile device over an internet connection, where the emergency alert comprises mobile device hybrid location data generated by the mobile device and a mobile device identifier;
      pushing the emergency alert comprising the mobile device hybrid location data and the mobile device identifier to an instance based on the mobile device hybrid location data and displaying the emergency alert on a GUI associated with the instance at a PSAP;

receive protected medical profile data corresponding to at least one patient medical identifier associated with the mobile device identifier contained in the emergency alert; and display an anonymized candidate profile list in the GUI at the PSAP having at least one list entry for the medical profile corresponding to the at least one patient medical identifier, the anonymized candidate profile not exposing protected medical information related to the patient medical identifier.

10. The emergency data manager of claim 9, wherein the processor is further operative to:

retrieve protected data comprising one or more anonymized candidate profiles corresponding to the patient identifier, the anonymized candidate profiles providing anonymized patient information without exposing protected data related to the patient.

11. The emergency data manager of claim 9, wherein the processor is further operative to:

receive a medical data request from an emergency responder mobile device associated with the PSAP and dispatched to a location based on the mobile device hybrid location data, the medical data request comprising the patient identifier and authentication data for the responder mobile device; and provide the protected medical information related to the patient medical identifier to the emergency responder mobile device in response to the medical data request and based on an authorization level specified in the authentication data to comply with access requirements for the protected medical information data.

12. The emergency data manager of claim 10, wherein the processor is further operative to:

display the anonymized candidate profiles on a display of the emergency responder mobile device in response to the medical data request;

receive a selection input corresponding to a selected one of the anonymized candidate profiles; and display non-anonymized protected medical information corresponding to the selected one of the anonymized candidate profiles on the display of the emergency responder mobile device in response to the selection input.

13. The emergency data manager of claim 12, wherein the processor is further operative to:

retrieve and transmit the non-anonymized protected medical information in compliance with requirements for protection of personally identifiable information (PII) and protected health information (PHI).

14. The emergency data manager of claim 9, wherein the processor is further operative to:

receive the patient medical identifier from a device of a bystander caller.

15. The emergency data manager of claim 9, wherein the processor is further operative to:

receive the medical data request from the emergency responder mobile device, the medical request comprising emergency responder credentials; and provide limited access to the protected data by the emergency responder mobile device based on data access limitations specified in the emergency responder credentials.

16. The emergency data manager of claim 9, wherein the processor is further operative to:

receive the medical data request from the GUI at the PSAP on behalf of the emergency responder mobile device, the medical data request comprising emergency responder credentials; and provide limited access to the protected medical information by the emergency responder mobile device based on data access limitations specified in the emergency responder credentials.

* * * * *